(12) United States Patent
Lutz et al.

(10) Patent No.: US 7,648,508 B2
(45) Date of Patent: Jan. 19, 2010

(54) BONE PLATING IMPLANTS, INSTRUMENTS AND METHODS

(75) Inventors: Christian Lutz, Solothurn (CH); Yves Crozet, Bellach (CH); Rene Wirth, Solothurn (CH)

(73) Assignee: Stryker Trauma S.A. (CH)

( * ) Notice: Subject to any disclaimer, the term of this patent is extended or adjusted under 35 U.S.C. 154(b) by 739 days.

(21) Appl. No.: 10/999,665

(22) Filed: Nov. 30, 2004

(65) Prior Publication Data
US 2006/0116679 A1  Jun. 1, 2006

(51) Int. Cl.
A61F 5/00 (2006.01)
(52) U.S. Cl. .................. 606/86 R; 606/281; 606/86 B
(58) Field of Classification Search ............ 606/96–98, 606/102, 915, 280–299, 70, 71, 166, 167, 606/172; 33/512
See application file for complete search history.

(56) References Cited

U.S. PATENT DOCUMENTS

| | | | |
|---|---|---|---|
| 2,932,296 A * | 4/1960 | Sanders | 606/167 |
| 3,547,114 A | 12/1970 | Haboush | |
| 3,765,034 A * | 10/1973 | Johnston | 623/22.4 |
| 4,667,664 A | 5/1987 | Taylor et al. | |
| 4,726,808 A | 2/1988 | Collins | |
| 5,085,660 A | 2/1992 | Lin | |
| 5,190,544 A | 3/1993 | Chapman et al. | |
| 5,207,682 A | 5/1993 | Cripe | |
| 5,207,683 A | 5/1993 | Goode et al. | |
| 5,334,192 A | 8/1994 | Behrens et al. | |
| 5,586,985 A * | 12/1996 | Putnam et al. | 606/86 B |
| 5,601,553 A | 2/1997 | Trebing et al. | |
| 5,620,449 A | 4/1997 | Faccioli et al. | |
| 5,681,265 A | 10/1997 | Maeda et al. | |
| 5,709,686 A | 1/1998 | Talos et al. | |
| 5,797,966 A | 8/1998 | Bontoux et al. | |
| 5,885,210 A | 3/1999 | Cox | |
| 5,897,557 A * | 4/1999 | Chin et al. | 606/71 |
| 5,954,722 A | 9/1999 | Bono | |
| 6,096,040 A | 8/2000 | Esser | |
| 6,099,547 A | 8/2000 | Gellman et al. | |
| 6,129,730 A | 10/2000 | Bono et al. | |

(Continued)

FOREIGN PATENT DOCUMENTS

DE  4341980  6/1995

(Continued)

OTHER PUBLICATIONS www.koenigsee-implantate.de, Angle Stable Humerous Plate, Aug. 6, 2004.

(Continued)

Primary Examiner—Thomas C Barrett
Assistant Examiner—Andrew Yang
(74) Attorney, Agent, or Firm—Lerner, David, Littenberg, Krumholz & Mentlik, LLP

(57) ABSTRACT

Bone plating implants, instruments, systems and methods for fracture fixation are provided. The systems includes the instruments and implants comprising a trial component, handle, aiming block, bone plate, tissue spreader, drill guide, K-wire guide, monoaxial screw-locking inserts, polyaxial screw-locking inserts, cable plugs, K-wires, monoaxial screws and polyaxial screws. The methods include the use of the instruments and implants for either open or minimally invasive fracture fixation surgery.

43 Claims, 8 Drawing Sheets

U.S. PATENT DOCUMENTS

| | | | |
|---|---|---|---|
| 6,166,666 | A | 12/2000 | Kadyk |
| 6,193,721 | B1 | 2/2001 | Michelson |
| 6,224,601 | B1 | 5/2001 | Friedl |
| 6,258,092 | B1 | 7/2001 | Dall et al. |
| 6,270,499 | B1 | 8/2001 | Leu et al. |
| 6,306,136 | B1 | 10/2001 | Baccelli et al. |
| 6,322,562 | B1 | 11/2001 | Wolter |
| 6,358,250 | B1 | 3/2002 | Orbay |
| 6,364,882 | B1 | 4/2002 | Orbay |
| 6,364,883 | B1 | 4/2002 | Santilli |
| 6,383,186 | B1 | 5/2002 | Michelson |
| 6,393,783 | B2 | 5/2002 | Emaus et al. |
| 6,413,259 | B1 | 7/2002 | Lyons et al. |
| 6,416,528 | B1 | 7/2002 | Michelson |
| 6,428,542 | B1 | 8/2002 | Michelson |
| 6,440,135 | B2 | 8/2002 | Orbay et al. |
| 6,454,770 | B1 | 9/2002 | Klaue et al. |
| 6,454,771 | B1 | 9/2002 | Michelson |
| 6,468,278 | B1 | 10/2002 | Muckter et al. |
| 6,508,819 | B1 | 1/2003 | Orbay |
| 6,520,907 | B1 | 2/2003 | Foley et al. |
| 6,527,776 | B1 | 3/2003 | Michelson |
| 6,530,926 | B1 | 3/2003 | Davison |
| 6,592,586 | B1 | 7/2003 | Michelson |
| 6,602,256 | B1 | 8/2003 | Hayes |
| 6,605,090 | B1 | 8/2003 | Trieu et al. |
| 6,620,163 | B1 | 9/2003 | Michelson |
| 6,623,486 | B1 | 9/2003 | Weaver et al. |
| 6,626,486 | B2 | 9/2003 | Lane et al. |
| 6,656,189 | B1 | 12/2003 | Wilson et al. |
| 6,669,701 | B2 | 12/2003 | Steiner et al. |
| 6,673,076 | B2 | 1/2004 | Deloge et al. |
| 6,692,503 | B2 | 2/2004 | Foley et al. |
| 6,695,844 | B2 | 2/2004 | Bramlet et al. |
| 6,706,045 | B2 | 3/2004 | Lin et al. |
| 6,706,046 | B2 | 3/2004 | Orbay et al. |
| 6,712,818 | B1 | 3/2004 | Michelson |
| 6,712,820 | B2 | 3/2004 | Orbay |
| 6,719,759 | B2 | 4/2004 | Wagner et al. |
| 6,730,090 | B2 | 5/2004 | Orbay et al. |
| 6,730,091 | B1 | 5/2004 | Pfefferle et al. |
| 6,746,450 | B1 | 6/2004 | Wall et al. |
| 6,746,453 | B2 | 6/2004 | Deloge et al. |
| 6,767,351 | B2 | 7/2004 | Orbay et al. |
| 6,926,720 | B2 | 8/2005 | Castaneda |
| 6,945,974 | B2 * | 9/2005 | Dalton ............ 606/70 |
| 7,083,624 | B2 * | 8/2006 | Irving ............ 606/87 |
| 7,128,744 | B2 | 10/2006 | Weaver et al. |
| D532,515 | S | 11/2006 | Buttler et al. |
| 7,175,631 | B2 | 2/2007 | Wilson et al. |
| 7,175,633 | B2 | 2/2007 | Roth et al. |
| 2002/0156474 | A1 | 10/2002 | Wack et al. |
| 2003/0014068 | A1 | 1/2003 | Bonutti et al. |
| 2003/0040748 | A1 | 2/2003 | Aikins et al. |
| 2003/0191371 | A1 | 10/2003 | Smith et al. |
| 2003/0199884 | A1 | 10/2003 | Davison et al. |
| 2004/0030339 | A1 | 2/2004 | Wack et al. |
| 2004/0059334 | A1 | 3/2004 | Weaver et al. |
| 2004/0059335 | A1 | 3/2004 | Weaver et al. |
| 2004/0078051 | A1 | 4/2004 | Davison et al. |
| 2004/0082960 | A1 | 4/2004 | Davison |
| 2004/0102778 | A1 | 5/2004 | Huebner et al. |
| 2004/0102788 | A1 | 5/2004 | Huebner et al. |
| 2004/0122429 | A1 * | 6/2004 | Phillips et al. ............ 606/69 |
| 2004/0133201 | A1 | 7/2004 | Shluzas et al. |
| 2004/0158246 | A1 * | 8/2004 | Assaker et al. ............ 606/61 |
| 2005/0049594 | A1 | 3/2005 | Wack et al. |
| 2006/0095044 | A1 | 5/2006 | Grady et al. |
| 2006/0116679 | A1 | 6/2006 | Lutz et al. |

FOREIGN PATENT DOCUMENTS

| | | |
|---|---|---|
| DE | 9321544 | 9/1999 |
| DE | 101 31 992 | 1/2003 |
| EP | 0 468 192 | 1/1992 |
| EP | 0 951 868 | 10/1999 |
| EP | 1211992 | 6/2002 |
| EP | 1 250 892 | 10/2002 |
| EP | 1 275 348 | 1/2003 |
| EP | 1284662 | 2/2003 |
| EP | 1661525 | 5/2006 |
| WO | WO-94/17744 | 8/1994 |
| WO | WO-2004/006802 | 1/2004 |
| WO | WO-2004/045389 | 6/2004 |
| WO | WO-2006050507 | 5/2006 |

OTHER PUBLICATIONS

Gotfried, Y., The Gotfried PC.C.P for Percutaneous Compression Plating of Pertrochanteric Hip Fractures, Operative Technique publication, date not known, 26 pages, available on the Internet at www.orthofox.com/ofus/pdf/gotfried-optech.pdf.

Synthes, 4.5 mm LCP Condylar Plate Instrument and Implant Sets, Internet brochure, date not known, 4 pages, available on the Internet at http://products.synthes.com/prod_support/support.asp.

Synthes, Less Invasive Stabilization System (LISS), Technique guide publication, Internet brochure, date not known, 34 pages, available on the Internet at http://products.synthes.com/prod_support/support.asp.

Synthes, 3.5 mm LCP Proximal Humerus Plate, Technique guide publication, Internet brochure, date not known, 10 pages, available on the Internet at http://products.synthes.com/prod_support/support.asp.

* cited by examiner

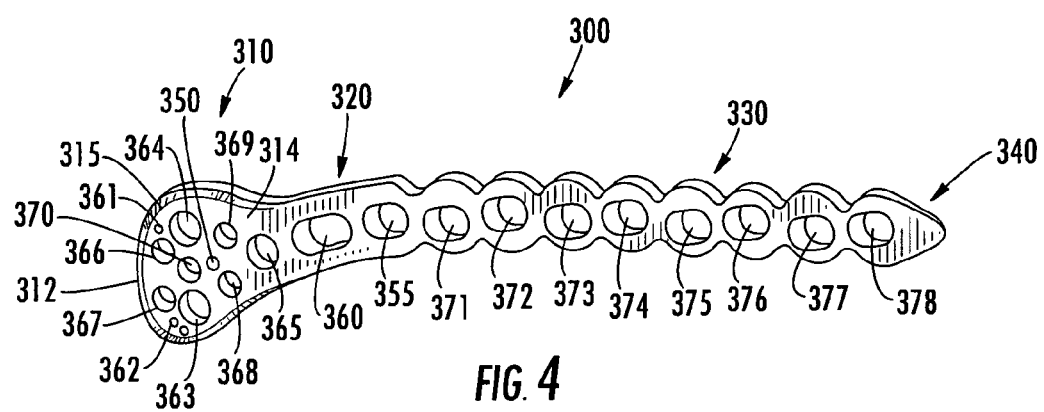
FIG. 4
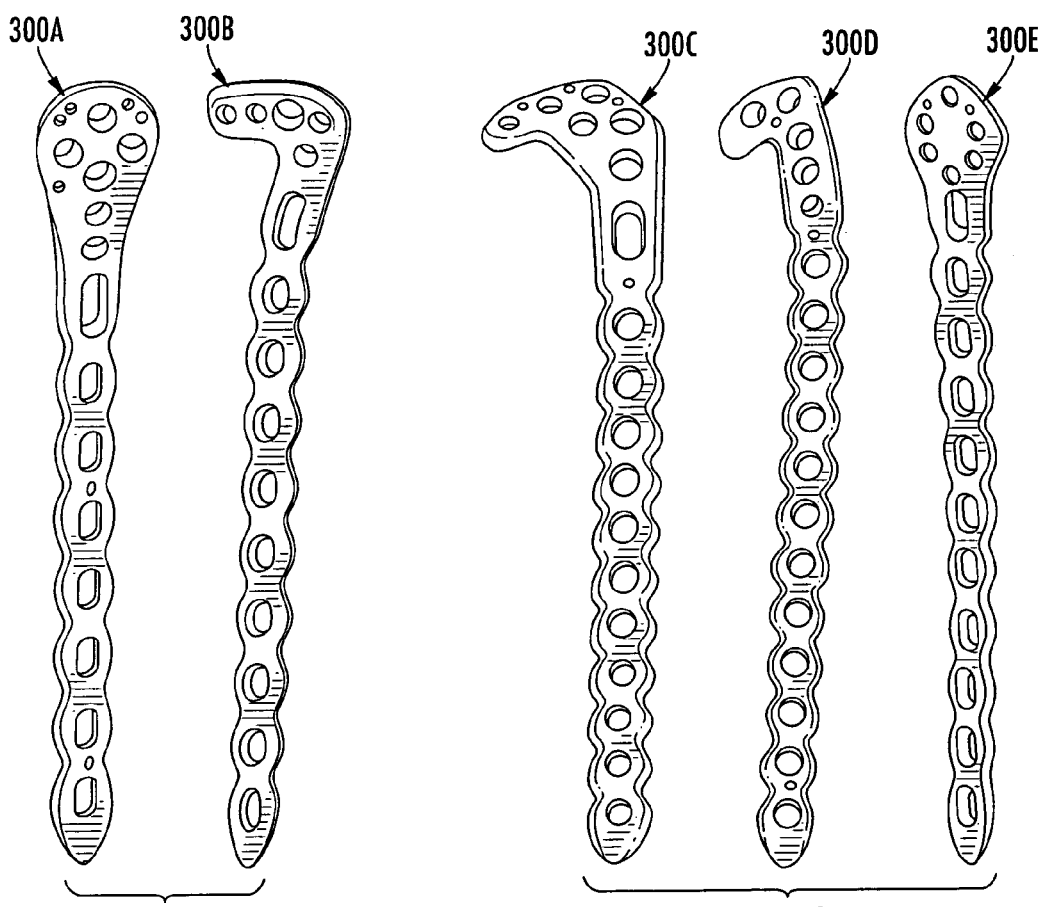
FIG. 5
FIG. 6

BONE PLATING IMPLANTS, INSTRUMENTS AND METHODS

BACKGROUND OF THE INVENTION

The present invention relates to a bone plating system and instrumentation used in the fixation of fractures of long bones such as the femur, tibia, humerus and radius, including peri-articular fractures. More specifically, the present invention encompasses a bone plating system that aids in preoperative planning of plate selection and placement, intraoperative adjustment and fixation of the plate to the fractured bone, as well as implementation in minimally invasive surgery, hereinafter referred to as MIS.

Typical fixation of a fracture of a long bone with a bone plate requires making an incision in the tissue, reducing the fracture, placing a bone plate on the fractured bone, and securing the bone plate to the bone with fixation elements such as screws. The bone plate immobilizes the fracture and keeps the bone in a correct position so as to allow the fracture to heal.

Typically, bone plates have a bone contacting side and a side facing away from the bone with a plurality of holes or apertures extending between the two surfaces. These holes or apertures may be either threaded (for use with locking screws) or non-threaded (for use with regular screws) and may be circular or oblong in shape.

One such bone plate is shown in U.S. Pat. No. 6,623,486 in which the plate has a head portion for placement adjacent the metaphysis of the bone and a shaft portion for placement against the diaphysis of the bone. The plate includes both locking (threaded) holes and non-locking holes. The locking holes are adapted to receive bone screws with threaded heads or proximal areas which engage the threads in the locking holes to thereby lock the screw to the plate. Bone screws without threaded heads can be then inserted into the non-locking holes or into the oblong holes which oblong holes permit the screws to be oriented at various angles.

The non-threaded holes can accommodate threaded inserts which can couple the bone screws to the plate via the engagement of the outer bone screw threads with inner threads on the inserts. See, for example, U.S. Pat. No. 5,954,722. In addition, the bone plate holes can accommodate inserts adapted to receive cerclage wires. An example of such an insert is shown in U.S. Pat. No. 5,190,545.

One difficulty involved with the use of locking screws in minimally invasive, or other surgery, is that such a screw must be accurately aligned with the threaded hole in the plate upon insertion to prevent cross threading of the engaging threads. One way of achieving this alignment is by using guide wires such as Kirshner wires (K-wires) and locating them within the bone plate holes. Cannulated bone screws are then placed over the wires which, if accurately positioned, guide the threaded portion of the screw to engagement with the threaded plate hole in the proper alignment. Placement of the guide wires may thus become a critical aspect of the procedure.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

One of the difficulties involved with the implantation of a bone plate is determining the correct size of the bone plate to be used, as well as the position in which it is to be affixed to the bone. Commonly, a non-invasive scan of the fracture, such as an x-ray, will serve as the template by which a surgeon must select the appropriately sized bone plate, and determine where it should optimally be affixed to the bone. Based on this preoperative assessment, intraoperatively, the surgeon must then position the plate on the bone and affix it in the predetermined optimal position. Because the surgeon may only have the x-ray to refer to intraoperatively, the placement of the plate and the drilling of corresponding bone screw holes with correct trajectories for monoaxial screws leaves room for inaccuracy and less than optimal fixation.

Another difficulty involved with the implantation of a bone plate is holding and manipulating a long, slim plate in an incision during the implantation procedure.

Yet another issue with the implantation procedure is the size of the incision. Although it is known that tissue may be stretched, common incisions generally span the length of the bone plate to be implanted. This is because of the visualization that is required for proper alignment of the bone plate, as well as drilling of bone screw holes, and implantation of bone screws.

Since it is desirable to minimize scarring and disruption of blood supply to the muscles through the use of smaller incisions, as well as increase the speed and accuracy of surgical procedures, MIS techniques are becoming more popular. However, present implantation techniques, as described above, present challenges in terms of utilizing smaller incisions, providing faster operating times, and maintaining or improving ease of handing of bone plates, as well as accurately fixating them to bone. Thus, there is a need in the art for implants, instruments and methods that facilitate accomplishing these objectives.

SUMMARY OF THE INVENTION

In one aspect of the preferred embodiment of the present invention there is provided a trial component that is used to aid in selecting a bone plate from a plurality of bone plates, for implantation and fixation of a fracture of a bone, based on an evaluation of the fractured bone together with the trial component.

The trial component has a shape that generally corresponds to the longitudinal shape of the fractured bone, and has a head and a stem. The trail component may, for example, have a shape resembling a femur.

The trial component also has a first side facing a fractured bone and a second side facing away from the bone. The first side aids in selecting a right bone plate for use in fixation of the right femur, while the second side aids in selecting a left bone plate for use in fixation of the left femur.

The trial component is preferably at least in part radiolucent.

In one aspect of the preferred embodiment of the trial component, the stem has radiopaque markers indicating different bone plate lengths. When the trial component is superimposed over a fractured bone, and an image of the fracture, such as through the use of fluoroscopy, is acquired, the radiopaque plate length markers are visible over the fractured bone in the image. This facilitates selection of the desired bone plate for use in fixation of the fracture.

In another aspect of the preferred embodiment of the trial component, the stem of the trial component, and optionally the head, have markers indicating the relative positions of screw holes in corresponding bone plates, and the stem of the trial component further has at least one slot. These markers may, optionally, be radiolucent so as to be visible along with the plate length markers in an image of the trial component over a fractured bone, but the stem markers, particularly, are used in connection with the slot when the trial component is used as an incision locator.

The centerline of the slot is defined by the centers of at least two adjacent radiopaque markers on the stem that indicate positions of screw holes in a bone plate. Thus, the slot is surrounded at least in part by radiopaque markers which indicate screw holes, but may also include markers which indicate the lengths of bone plates. The width of the slot facilitates insertion of a scalpel therethrough, and the surrounding screw hole markers indicate locations for incisions so that the incisions can be made above the corresponding holes in the bone plate. Multiple such slots may be located on the stem.

In yet another aspect of an embodiment of the trial component, the head of the trial component has an opening for receiving a handle of the present invention. The opening is adjacent to a movable locking element, or slider, which comprises a tongue and a tab. The opening has an edge which is opposite the tongue. The tongue is oriented generally parallel to the trial component, and the tab, which is configured to be pushed by a user's hand, is oriented generally transverse to the tongue. The slider is slidably connected with the head of the trial component, and is configured to move with respect to the opening so as to make the opening larger and smaller.

An open position for the slider is defined by the opening being larger, and a closed position for the slider is defined by the opening being smaller. The slider is biased, such as by a spring, in the closed position, and together with the edge of the opening, is adapted for engaging and securing the handle to the trial component when in the closed position, while facilitating movement of the handle through the opening when in the open position.

In another aspect of the preferred embodiment of the present invention there is provided a handle for positioning the trial component adjacent a fractured bone, and for manipulating and inserting a bone plate, such as an axially extending bone plate, into a fracture site.

In one aspect of an embodiment of the handle, the handle has a body with a first end, a second end, and an intermediate portion extending therebetween. The intermediate portion may be in the form of a shell, and may, for example, be comprised of a series of circumferentially interrupted vertical steps made up of extensions and recesses. The intermediate portion facilitates attachment of the trial component to the handle, wherein the tongue and edge of the trial component may securely and releasably fit into any of the recesses along the height of the intermediate portion of the handle, and with the slider of the trial component in the closed position, prevent the trial component from moving upwardly or downwardly along the handle. Advantageously, the trial component may be rotated around the handle while seated in a selected recess on the handle. This is facilitated by interaction between the circumferential interruption of the recess, along with the spring biased slider and the edge of the opening of the trial component, wherein during rotation, there is contact between the circumferential step, with the slider and edge of the trial component.

In another aspect of an embodiment of the handle, the second end of the handle is adapted for releasable connection to a bone plate to facilitate manipulating the bone plate and inserting it into a fracture site. The second end has an interface section that houses a connector which ultimately facilitates attachment of the handle to the bone plate. The interface section is adapted for engagement with a connection element, such as an aiming block, via the connector and optionally, at least one groove, and the aiming block is adapted for engagement with the bone plate.

The connector may be a spring loaded pin that is biased outwardly with respect to the handle. A biased actuator, or plunger, is also provided on the first end of the handle, which extends to the second end, and facilitates actuation and movement of the biased pin inwardly and outwardly with respect to the handle, for disengagement and engagement with the bone plate through releasable attachment to the aiming block, for example. Intermediate the connection between the plunger and pin may be a biased member such as a plug that facilitates actuation of the pin. The plunger, plug, and pin, along with the interacting biasing forces such as springs, may be termed an actuating mechanism.

In another aspect of the preferred embodiment of the present invention there is provided an aiming block that facilitates attaching the handle to the bone plate, as well as orienting a drill guide and/or Kirshner wire (K-wire) guide relative to the bone plate, to enable the guides to be used accordingly. The aiming block has a top surface facing away from the bone plate, a bottom surface facing toward the bone plate, and a side surface intermediate the top and bottom surfaces.

In one aspect of an embodiment of the aiming block, on the bottom surface, the aiming block further has a chamfer which mates with a chamfer on the top surface of the head of the bone plate. The configuration of the aiming block's chamfer and bottom surface with respect to the bone plate's chamfer and top surface is such that when the block and plate are assembled, there is a gap between the surfaces. This gap allows for manufacturing variations in the surfaces of both the block and plate to not interfere with the functionality and interaction between the two parts.

Advantageously, the aiming block has a plurality of through-holes that correspond to a plurality of holes in the head of the bone plate. Some of the aiming block's holes are configured for receiving a drill guide, while some are configured for receiving a K-wire guide. At least one hole in the block is configured for receiving a screw that is to connect the block to the head of the bone plate.

In another aspect of an embodiment of the block, this screw hole is non-threaded, and the screw is partially threaded. The non-threaded portion of the partially threaded screw is in contact with the non-threaded hole in the block after the screw is put through the hole and threaded into the bone plate, thus attaching the block to the plate.

In still another aspect of an embodiment of the block, the block may be configured for use with monoaxial screws. As such, the through-holes in the block have particular trajectories that coincide with trajectories of corresponding holes in the bone plate.

In yet another aspect of an embodiment of the block, the block may be configured for use with polyaxial screws. As such, the through-holes in the block are conically shaped such that their openings taper down from the top surface to the bottom surface of the block.

In still another aspect of an embodiment of the block, the block may have an attachment interface, such as an extension, attached thereto. The extension facilitates securely and releasably connecting the block to the handle. With the block connected to the bone plate, the extension may be oriented such that it enables the connected handle to generally be a continuation of the plate, but at an angle thereto.

In one aspect of an embodiment of the extension, the extension may be formed by two rails separated by a channel that has a dimple. The extension is adapted for secure and releasable connection with the interface section of the second end of the handle via interaction between the rails and dimple of the block with the grooves and biased pin of the handle, respectively. In attaching the handle to the block, the rails are slipped into the grooves, and the pin rides along the channel, until the pin engages the dimple, at which point the biased pin snaps into the dimple. In this manner, the handle gets securely and releasably attached to the block.

In another aspect of an embodiment of the handle, the actuating mechanism of the handle facilitates release of the handle from the block. Release is accomplished by pressing the biased plunger down toward the handle. Through the actuating mechanism, this removes the biasing force that pushes the pin outwardly from the handle, and allows a counteracting weaker biasing force around the pin to move the pin inwardly. At that point, the handle may be freely separated from the extension of the block.

In yet another aspect of the preferred embodiment of the present invention there is provided a tissue spreader for engaging and enlarging an incision in tissue. The tissue spreader has first and second, or left and right, handles that are pivotally coupled to each other. The handles have respective first ends and second ends. The second ends of the handles are each attached to a transversely oriented tissue-engaging blade.

The tissue spreader further has a bar that also has a first end and a second end that is attached to a transversely oriented tissue-engaging blade, similar to the left and right handles. The bar is disposed between the handles, and is movable therebetween by actuation and movement of the left and right handles towards each other.

In one aspect of the preferred embodiment of the tissue spreader, the bar may be slidably connected to the left and right handles via a pin that pivotally connects the handles together. The pin may reside in a slot of the bar, and the bar, at its first end, may be further connected to the left and right handles via links such as a left link and right link. Upon actuation and rotational movement of the left and right first ends of the left and right handles toward each other, the bar gets translationally drawn away from the left and right second ends of the left and right handles.

In another aspect of the preferred embodiment of the tissue spreader, the tissue-engaging blades of the left and right handles, together with the tissue-engaging blade of the bar, form a tube that has a proximal end closest to the second ends of the handles, and a distal end opposite the proximal end. When the tissue spreader is in the closed position, the tube has an enclosed passage that is defined by the blades. This passage is conical, and tapers from a larger cross-section at the proximal end, to a smaller cross-section at the distal end. Advantageously, the blades may have outwardly oriented lips on their distal ends that facilitate engaging and retaining tissue during the tissue's retraction by the tissue spreader.

When the tissue spreader is in the closed position, the first ends of the handles are farthest apart from each other, and the three blades are closest to each other, such that the three blades form the tube with a narrow passage therethrough. Actuation of the handles, or movement of the first ends of the handles towards each other, causes the left and right blades to move away from each other, and causes the bar to translate away from the left and right blades, thus causing the bar's blade to move away from the left and right blades, and expanding the passage in the tube. In the resulting open position of the tissue spreader, the first ends of the handles are closest to each other, and the three blades are farthest from each other, thus forming a wide passage therebetween.

In use, when the tissue spreader is in the closed position, the tube is inserted into the incision in a patient. The tissue spreader is then actuated, and the incision is enlarged by the movement of the three blades away from each other.

In yet another aspect of the preferred embodiment of the tissue spreader, there is provided a retaining mechanism such as a ratchet and pawl, that is attached to the left and right handles. The retaining mechanism facilitates selectively and releasably maintaining the tissue spreader in any open, closed, or intermediate position. Leaf springs, which may be attached to the handles, bias the handles in the closed position, and facilitate improved operation of the retaining mechanism by providing a biasing force in conjunction therewith.

The ratchet mechanism may be attached to the handles intermediate the handles' first ends and the pivot point. Alternatively, the ratchet mechanism may be attached at the handles' first ends.

In yet another aspect of a preferred embodiment of the present invention, bone plates may be provided with one or more holes, in either the head and/or stem of the plate, that facilitate insertion and retention of either monoaxial screw locking inserts or polyaxial screw locking inserts.

In still another aspect of the preferred embodiment of the present invention there is provided a cable plug adapted for placement in the holes of a bone plate. The cable plug facilitates attachment of cables or wires to the bone plate. In one aspect of an embodiment of the cable plug, the cable plug has a cap, shank and connector, such as a bead. The shank is adapted for insertion into a bone plate hole, the bead, which may be nylon or a spring detent, is adapted to retain the plug in the hole, and the head is adapted to at least partially cover the hole while providing an attachment surface for cables or wires. Advantageously, the bead may be made from nylon, but other materials that serve the purpose of retaining the cable plug in the bone plate hole are also envisioned. In an alternate embodiment of the cable plug, the connector may be a nylon washer affixed to the end of the shank.

Another aspect of a preferred embodiment of the present invention is a system or kit that facilitates implantation of a bone plate for the purpose of fracture fixation. The system or kit comprises the aiming block and handle, but may also include the trial component, as well as a drill guide, K-wire guide, bone plate, tissue spreader, K-wires, monoaxial screws, polyaxial screws, monoaxial locking inserts, polyaxial locking inserts, and cable plugs, as described above and herein.

Optionally, the bone plate may be one of multiple bone plates with varying lengths, and may be for use with fixation of a femur, tibia, humerus, radius, including periarticular fractures for example. The aiming block may be one of a left or right aiming block, and may be configured for use with monoaxial or polyaxial screws, as well as configured to approximate and be attached to the head of the selected bone plate. The handle is attachable to the aiming block, and the trial component, the shape of which approximates the fractured bone to be fixed. The tissue spreader is configured for enlarging an incision in the patient's tissue. The monoaxial and polyaxial locking inserts, as well as the cable plugs are configured for attachment to holes in the bone plate, and the monoaxial and polyaxial screws are configured for attaching the bone plate to the fractured bone.

Another aspect of a preferred embodiment of the present invention is a method of stabilizing a fractured bone with a bone plate. The method comprises the steps of selecting a trial component corresponding to the shape of the fractured bone, placing the trial component adjacent the soft tissue surrounding the fracture, obtaining an image, such as with fluoroscopy, of the trial component and fracture, determining a desired bone plate size for implantation and fixation of the fracture based on evaluation of the trial component and fractured bone in the image, and implanting the selected bone plate to stabilize the fractured bone. Optionally, the method may also include, prior to implantation of the bone plate, any one or more of the following steps, such as: selecting a bone plate from a set of bone plates having varying lengths; determining which holes in the bone plate will receive inserts, as well as which types of inserts, such as monoaxial locking inserts, polyaxial locking inserts and/or cable plugs; inserting the selected inserts into the selected holes in the bone plate; selecting one of a left or right aiming block that corresponds with the selected bone plate; releasably attaching the selected aiming block to the head of the selected bone plate with a screw; releasably attaching a handle to the aiming block; manipulating the bone plate with the aiming block and placing it in position over the fracture; using a K-wire guide to place K-wires through the aiming block and bone plate; using a drill-guide to place screws through the aiming block and attach the bone plate to the bone; attaching the trial component to the handle by moving the slider on the trial component to the open position, putting the handle through the opening in the trial component, and releasing the slider thus securing the trial component to the handle; making select incisions through the slots in the trial component corresponding to the desired holes in the plate that are to receive screws, the positions of the incisions being identified on the trial component by radiopaque hole markings thereon which correlate with holes in the plate; rotating the trial component out of the way of the incision, or separating it from the handle; inserting the tube of a closed tissue spreader into an incision; actuating the spreader to enlarge the incision by separating the blades of the tissue spreader; inserting a screw through the incision and through the hole in the bone plate to attach the plate to the fractured bone; removing the tissue spreader from the incision; repeating the procedure of making incisions and inserting screws for all the selected holes in the bone plate that are to receive screws; disengaging the handle from the aiming block; disengaging the aiming block from the bone plate, and closing the one or more incisions.

BRIEF DESCRIPTION OF THE DRAWINGS

FIG. 4 is a top perspective view of a bone plate for use in fixing fractures of the distal lateral femur.

FIG. 5 is a top perspective view of one bone plate for use in fixing fractures of the proximal lateral humerus, and another for use in fixing fractures of the distal radius.

FIG. 6 is a top perspective view of three bone plate for use in fixing fractures of the proximal lateral tibia, distal anterior lateral tibia, and distal medial tibia, respectively.

Figure 1:
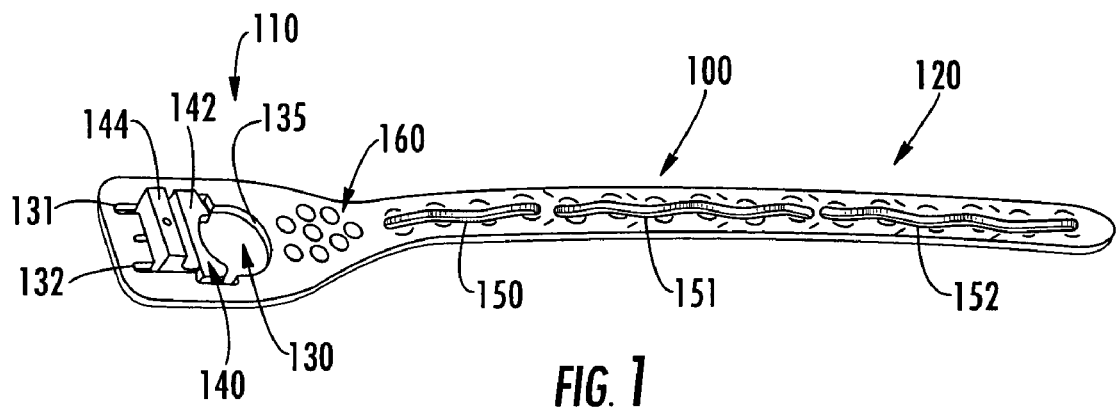
FIG. 1 is a top perspective view of a trial component with a slider attached.

| IDENTIFICATION OF ELEMENT NUMBERS | |
|---|---|
| 100 | trial |
| 110 | trial head |
| 120 | trial stem |
| 130 | opening |
| 131 | extension |
| 132 | extension |
| 133 | slot |
| 135 | edge of opening |
| 140 | slider |
| 142 | tongue |
| 144 | tab |
| 150 | slot |
| 151 | slot |

-continued

IDENTIFICATION OF ELEMENT NUMBERS

| | | |
|---|---|---|
| 152 | slot | |
| 160 | screw hole indicators | |
| 171 | screw hole indicators | |
| 172 | screw hole indicators | |
| 173 | screw hole indicators | |
| 174 | screw hole indicators | |
| 180 | plate size markers | |
| 181 | plate size markers | |
| 183 | plate size markers | |
| 183 | plate size markers | |
| 184 | plate size markers | |
| 185 | plate size markers | |
| 186 | plate size markers | |
| 200 | elevator | |
| 210 | hand grip | |
| 220 | shaft | |
| 230 | tip | |
| 300 | plate | |
| 310 | head | |
| 312 | end of the head | |
| 314 | top surface of the head | |
| 315 | chamfer | |
| 320 | neck | |
| 330 | stem | |
| 340 | tip | |
| 350 | small threaded hole | |
| 355 | regular screw hole in the stem of the plate | |
| 360 | positioning slot | |
| 361 | K-wire hole | |
| 362 | K-wire hole | |
| 363 | regular screw hole in the head of the plate | |
| 364 | regular screw hole in the head of the plate | |
| 365 | regular screw hole in the head of the plate | |
| 366 | locking screw hole in the head of the plate | |
| 367 | locking screw hole in the head of the plate | |
| 368 | locking screw hole in the head of the plate | |
| 369 | locking screw hole in the head of the plate | |
| 370 | locking screw hole in the head of the plate | |
| 371 | regular screw hole in the stem of the plate | |
| 372 | regular screw hole in the stem of the plate | |
| 373 | regular screw hole in the stem of the plate | |
| 374 | regular screw hole in the stem of the plate | |
| 378 | regular screw hole in the stem of the plate | |
| 300A | plate | |
| 300B | plate | |
| 300C | plate | |
| 300D | plate | |
| 300E | plate | |
| 400 | aiming block | |
| 410 | body | |
| 412 | end of the aiming block | |
| 420 | top surface | |
| 430 | side surface | |
| 440 | bottom surface | |
| 445 | chamfer | |
| 450 | attachment hole | |
| 461 | K-wire hole | |
| 462 | K-wire hole | |
| 463 | opening for regular screw hole | |
| 464 | opening for regular screw hole | |
| 465 | opening for regular screw hole | |
| 466 | opening locking screw hole | |
| 467 | opening locking screw hole | |
| 468 | opening locking screw hole | |
| 469 | opening locking screw hole | |
| 470 | opening locking screw hole | |
| 480 | extension | |
| 482 | rail | |
| 484 | rail | |
| 486 | channel | |
| 488 | dimple | |
| 500 | drill guide | |
| 510 | handgrip | |
| 520 | shaft | |
| 530 | threaded tip | |
| 550 | K-wire guide | |
| 560 | handgrip | |
| 570 | shaft | |
| 575 | split ring | |
| 578 | circular groove | |
| 580 | tip | |
| 600 | cable plug | |
| 610 | cap | |
| 620 | shank | |
| 630 | bead | |
| 700 | handle | |
| 710 | top of the handle | |
| 713 | section line | |
| 720 | shell | |
| 722 | steps | |
| 724 | extension | |
| 726 | recess | |
| 730 | bottom of the handle | |
| 732 | interface section | |
| 734 | screw | |
| 740 | plunger | |
| 742 | plunger cap | |
| 744 | plunger shaft | |
| 746 | plunger tip | |
| 750 | space | |
| 755 | spring | |
| 760 | plug | |
| 762 | plunger face of plug | |
| 764 | pin face of plug | |
| 765 | spring | |
| 768 | spring housing | |
| 770 | housing | |
| 780 | pin | |
| 784 | plug face of pin | |
| 785 | spring | |
| 788 | tip of pin | |
| 790 | groove | |
| 800 | tissue spreader | |
| 810 | left handle | |
| 811 | end | |
| 812 | hand grip section | |
| 813 | left link pivot point | |
| 814 | head of left handle | |
| 815 | left blade | |
| 816 | lip | |
| 820 | right handle | |
| 821 | end | |
| 822 | hand grip section | |
| 823 | right link pivot point | |
| 824 | head of right handle | |
| 825 | right blade | |
| 826 | lip | |
| 830 | handle hinge joint | |
| 832 | guide pin | |
| 840 | left bar | |
| 842 | pivot point | |
| 850 | right bar | |
| 852 | pivot point | |
| 860 | center bar | |
| 861 | tail | |
| 862 | body | |
| 863 | slot | |
| 864 | head | |
| 865 | center blade | |
| 866 | lip | |
| 870 | tube | |
| 872 | proximal end | |
| 874 | distal end | |
| 880 | passage contracted | |
| 885 | passage expanded | |
| 890 | ratchet | |
| 892 | pawl | |
| 895 | leaf springs | |
| 900 | leg | |
| 910 | femur | |
| 920 | fracture | |
| 930 | screw | |
| 940 | K-wire | |
| 950 | drill bit | |

-continued

IDENTIFICATION OF ELEMENT NUMBERS

| | |
|---|---|
| 955 | MIS incision |
| 970 | incision |
| 984 | regular screw |
| 988 | locking screw |
| 990 | screw |

DETAILED DESCRIPTION

Figure 2:
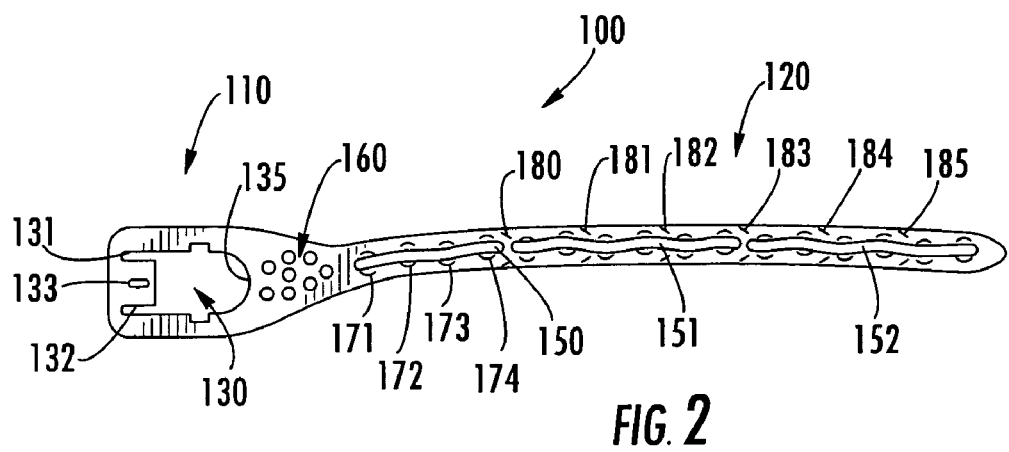
FIG. 2 is a top view of the trial component of FIG. 1 without the slider attached.
Figure 19:
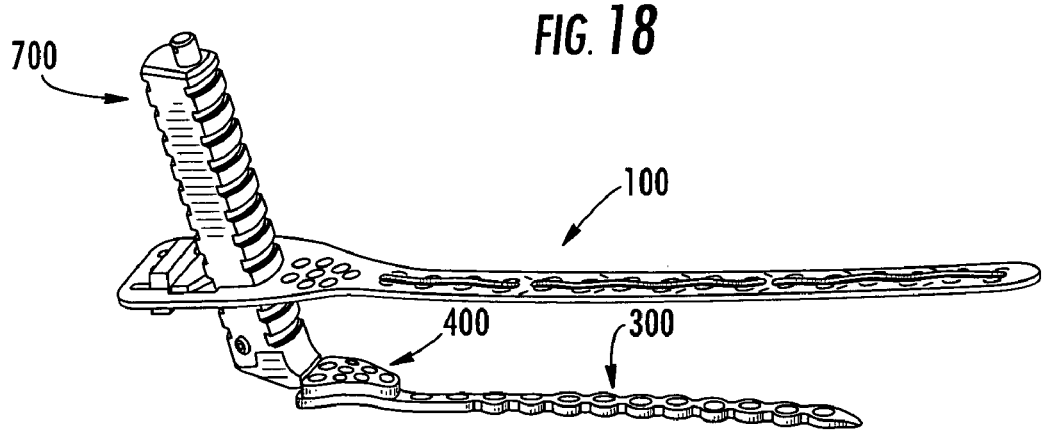
FIG. 19 is a side perspective plan view of the assembly of a trial component, handle, aiming block and bone plate as used in a surgical procedure.

With reference to FIGS. 1, 2 and 19, there is illustrated a preferred embodiment of a trial component 100 of the present invention. The trial component 100 has a head 110 and a stem 120. The orientation of the head 110 versus the stem 120, and the general shape of the trial 100 approximates the shape of a bone plate 300 to be used on the distal femur, as is recognized by those skilled in the art. Trial 100 is intended to be used with a correspondingly shaped bone plate 300 for the distal femur. One side of the trial 100 is for use with the left femur while, when flipped over, the other side is for use with the right femur. Trial and bone plate shapes and sizes that correspond to other long bones are equally envisioned, and will be recognized by those skilled in the art.

The head 110 of the trial 100 has an opening 130 therethrough, and a slider 140 cooperatively assembled with the opening 130. The opening 130 has two extensions 131 and 132, a slot 133 juxtaposed between the extensions 131 and 132, and an edge 135 which is located opposite the extensions 131, 132. The purpose of the opening 130, extensions 131 and 132, and slot 133 is to facilitate the assembly of the slider 140 with the plate 100, and to allow for the slider 140 to move in the opening 130 so as to increase and decrease the size of the opening 130.

The slider 140 has a horizontal tongue portion 142 and a vertical tab 144. The slider 140 is biased in the closed position such that the opening 130 is minimized. The purpose of the tab 144 is to provide a contact surface to enable a surgeon to move the slider 140 in the direction away from the trial stem 120 to thus enlarge the opening 130. At it's farthest point, the slider is in the open position such that the opening 130 is maximized. When the tab 144 is released, the slider 140 moves back to the closed position. The purpose of the tongue 142 and edge 135 of the opening 130 is to press against, and hold, a handle that will be positioned in the opening 130, as will be described in more detail below.

Closer to the stem portion 120 of the trial 100, trial head 110 also has various screw hole indicators 160 that are in the form of radiopaque markings on the surface of the trial head 110. As is known in the art, radiopaque markings may be formed by the addition of barium, but of course, other methods known to those skilled in the art are equally applicable. These indicators 160 identify the locations of the screw holes on the head portion of an actual bone plate that is to be implanted. Along with other radiopaque markers on the trial 100, these indicators 160 are intended to assist in preoperative planning of the fracture fixation surgery by being visible in a fluoroscopic image, and providing a surgeon with an approximation of where the corresponding bone plate holes would be oriented on the distal femur.

With particular reference to FIG. 2, trial stem 120 has multiple slots 150-152, as well as markers 171-174 and 180-186 on it. As with indicators 160, the markers 171-174 and 180-186 are radiopaque markings on the surface of the stem 120 of the trial 100. Screw hole markers 171-174 indicate the location of screw holes in a corresponding bone plate. Plate size markers 180-186 indicate the various lengths of corresponding bone plates that may be selected by the surgeon during preoperative planning. In fluoroscopy, all the markings are visible over the fractured bone, and enable a surgeon to select the size of the bone plate to be implanted, as well as visualize the position of that bone plate and its screw holes as juxtaposed over the fractured bone. The procedure for preoperative planning using the trial 100 will be discussed in more detail, below.

The shapes of the three slots 150-152 on the stem 120 of the trial 100 are determined by the center points of each screw hole marker. Thus, for example, the shape of slot 150 is determined by following a centerline that connects the centers of screw hole markers 171 with 172, 173 and 174. Although it is recognized that slots 150-152 may be formed as one continuous slot along stem 120, it is also recognized that one such long slot would weaken the structure of the stem 120 of the trial 100, and therefore may be undesirable. Alternatively, the slots may be of any length. The purpose of the slots is to allow a scalpel to be passed through so as to make an incision in the skin below the trial 100. This will be discussed in more detail in connection with the discussion of the methods of the present invention.

Figure 3:
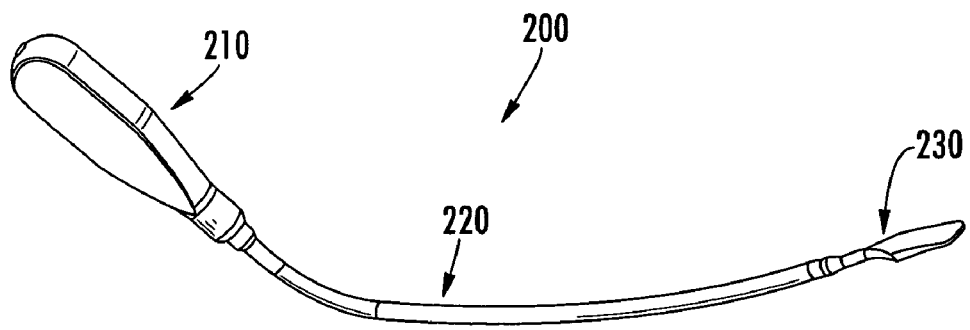
FIG. 3 is a side perspective view of an elevator tool used to elevate tissue in the area of implantation of a bone plate.

FIG. 3 illustrates a tissue elevator 200 that is well known to those skilled in the art. The elevator 200 has a handgrip 210, a shaft 220, and a tip 230. In surgery, the elevator 200 is held at handgrip 210, and is inserted into a first incision in the patient. The tip 230 is run along the bone in order to separate and elevate tissue away from the bone and make room for the bone plate that is to be inserted and implanted in that location.

FIG. 4 illustrates a preferred embodiment of a bone plate 300 of the present invention. As will be recognized by those skilled in the art, this bone plate 300 is shaped for use with the distal femur.

Plate 300 has a head 310, which has a chamfered edge 315, and terminates at an end 312, a neck 320, a stem 330, and a tip 340, which is opposite end 312. The tip 340 of the plate 300 is rounded and tapered to facilitate smooth insertion into the incision and under the soft tissue surrounding the implantation site. The chamfered edge 315, which is located on the top surface 314 of the head 310, is shaped to cooperatively assemble with an aiming block 400, as will be discussed in more detail, below.

The plate neck 320 has a slot 360 which is used to initially attach the plate 300 to the fractured bone, and permit a surgeon to adjust the position of the plate after checking initial plate placement using fluoroscopy. This method will be described in more detail, below.

The plate head 310 also has various openings. Opening 350 is a small threaded blind hole that is used for attaching an aiming block, which will be described below, to the head 310 of the plate 300. Openings 361 and 362 are through-holes that will accept K-wires, which are used in conjunction with fine-tuning the position of the plate 300 on the bone, as will be discussed in more detail, below. Openings 363-365 are through-holes that will accept regular bone screws which will attach the plate head 310 to the bone. Openings 366-370 are threaded through-holes that will accept either a self-guided locking screw or a regular bone screw which will attach the plate head 310 to the bone. Self-guided locking screws are disclosed in U.S. Patent Application entitled "Self-Guiding Threaded Fastener", with inventor Yves Crozet, filed on Nov. 30, 2004, the entire disclosure of which is incorporated herein by reference as if fully set forth herein. The locking feature of self-guided locking screws comes from the proximal portion of the locking screw, just below the head, having a larger thread diameter than the rest of the shaft of the screw. The communication of this larger thread with a threaded hole results in a locking of the screw to the hole, and consequently, to the plate.

The plate stem 330 has openings 355, 371-378 which are through-holes that will accommodate regular bone screws which will attach the plate stem 330 to the bone. In a preferred embodiment, the holes 355, 371-378 are oblong. Alternatively, threaded inserts may be inserted into the through-holes 355, 371-378. Threaded inserts are disclosed in U.S. patent application Ser. No. 10/803,638, entitled "Bone Connection Device", with inventors Volker Buhren and Christian Lutz, filed on Mar. 18, 2004, the entire disclosure of which is incorporated herein by reference as if fully set forth herein. The threaded inserts permit the use of locking screws, rather than regular screws to attach the bone plate 300 to the bone by providing a central opening having a inner threaded surface that communicates with the proximal threaded portion of a locking screw to provide the same locking capability as described above with respect to locking screws and threaded openings 366-370. It is also noted that different threaded inserts may similarly be employed with through-holes 363-365 in the head 310 of the plate 300.

In an alternative embodiment of the plate 300 (not shown), any or all of holes 355, 363-378 may be formed to accept inserts that facilitate the placement and locking of polyaxial screws. One such polyaxial locking insert is identified in U.S. Patent Application entitled "Device For Connecting a Screw to a Support Plate", with inventor Robert Porcher, filed on Nov. 29, 2004, the entire disclosure of which is incorporated herein by reference as if fully set forth herein. This insert is adapted for engagement with a hole in the plate 300, and contains a constriction ring having a through-hole and a non-circular outer profile which cooperates with a non-circular inner profile of the insert. When a screw is placed through the through-hole in the ring and turned along with the ring, the interference of the non-circular outer surface of the ring with the non-circular inner surface of the insert causes the ring to compress around the screw, thus locking the screw to the insert, and consequently to the plate.

Use of the bone plate 300 will be described in more detail, below.

FIGS. 5-6 illustrate other embodiments of bone plates of the present invention. As will be recognized by those skilled in the art, plates 300A-300E are shaped for use with corresponding bone segments, wherein plate 300A is for a proximal lateral humerus, 300B is for a distal radius, 300C is for a proximal lateral tibia, 300D is for a distal anterior lateral tibia, and 300E is for a distal medial tibia. Plates 300A-300E have generally similar holes and features as plate 300, except for the adaptation of these holes and features for use with the respective bone segments. It is noted that the discussions relating to plate 300 and its use are equally applicable to plates 300A-300E with obvious variations being readily apparent to those skilled in the art.

Figure 7:
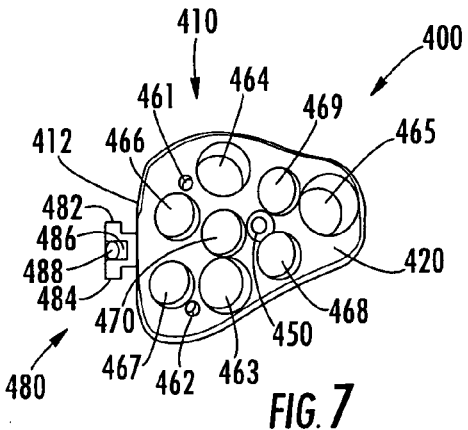
FIG. 7 is a top view of an aiming block used in conjunction with a bone plate, and particularly with the bone plate of FIG. 4.
Figure 8:
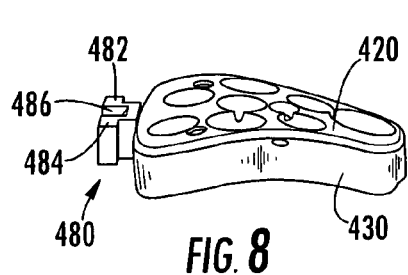
FIG. 8 is a side perspective view of the aiming block of FIG. 7.
Figure 9:
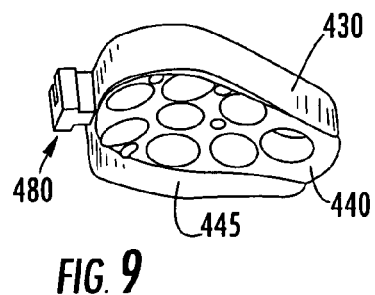
FIG. 9 is a bottom perspective view of the aiming block of FIG. 7.

FIGS. 7-9 illustrate a preferred embodiment of an aiming block 400 of the present invention. The purpose of the aiming block is to provide support and specific guidance to a drill guide that is used to form holes in the bone for screw placement in connection with attaching a bone plate to a bone. Because the bone plate 300 is affixed to the bone with monoaxial screws, it is important to prepare holes in the bone that accurately correspond to the bone plate holes, and that are properly oriented in the desired trajectories through the bone. Block 400 is, therefore, intended to be attached to the head 310 of the plate 300 to facilitate the proper preparation of bone screw holes in bone.

Block 400 has a body 410 that has an end 412. For reference and orientation of block 400 with respect to plate 300, end 412 is oriented generally over end 312 of bone plate 300.

Block 400 also has a top surface 420, side surface 430 and bottom surface 440. The top and bottom surfaces 420 and 430 are contoured to approximate the contour of the head 310 of plate 300, while a chamfer 445 on the bottom surface 440 of the block 400 is shaped to cooperatively mate with chamfer 315 of plate 300. The side surface 430 indicates the thickness of block 400.

Toward the middle of the top surface 420 of block 400, there is located a small through-hole 450 that corresponds with threaded hole 350 in the head 310 of plate 300, and facilitates connecting block 400 to plate 300 with a screw. Hole 450 is threaded to prevent the screw from separating from the block 400 while manipulating the block 400 before it is attached to the plate 300. The method of connecting the block 400 to the plate 300, as well as use of the block 400, will be discussed in more detail, below.

Block 400 also has two K-wire through-holes 461 and 462 that correspond to K-wire through-holes 361 and 362 in the head 310 of plate 300. Additionally, all the other through-holes 463-470 in block 400 correspond to associate holes 363-370 in the head 310 of plate 300. The trajectories of the smaller through-holes 466-470 in block 400 are aligned with the trajectories of through-holes 366-370 in the head 310 of plate 300. The larger holes 463-465 are configured to accept a regular drill guide that is used in connection with regular screws, while the smaller holes 466-470 are configured to accept and guide a different drill guide that is used in connection with self-guided locking screws. Drill guides will be discussed in more detail, below.

In an alternate embodiment, block 400 (not shown) may be used for placement of polyaxial screws through the head 310 of plate 300. The holes 463-470 of such block 400 are conically shaped with the larger diameter of the cones being on the top surface 420 of the block, and the smaller diameter of the cones being on the bottom surface 440 of the block 400. As a result of such conically shaped holes, drill guides placed within these holes will have a range of motion to facilitate selecting desired trajectories of the screws that will be implanted.

With continued reference to FIGS. 7-9, an extension is attached to the end 412 of block 400. The extension 480 has two rails, 482 and 484, a channel 486 in between rails 482 and 484, and, as best seen in FIG. 7, a dimple 488. The particular geometry of extension 480 is adapted to matingly interact with a handle of the present invention, which will be described below, to enable improved handling and manipulation of plate 300 in an incision. Of course, it is recognized that other configurations of the extension 480, as well as other configurations that will enable attachment to a handle, are envisioned.

Figure 10:
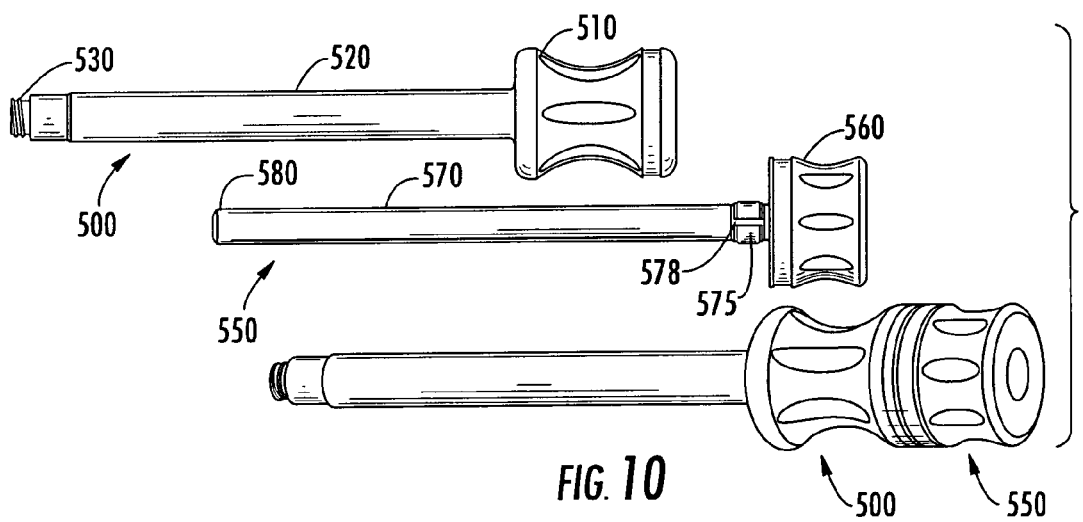
FIG. 10 is a side perspective view of a drill guide with K-wire guide used in conjunction with an aiming block and a bone plate, to prepare a hole in a bone for placement of a screw.

FIG. 10 illustrates a preferred embodiment of a drill guide 500 and a K-wire guide 550 of the present invention, as well as their assembly. As is well known to those skilled in the art, drill guides are used to guide a drill bit into the bone to form a hole for implantation of a bone screw, while k-wire guides are used to guide k-wires.

Drill guide 500 features a handgrip 510, shaft 520, and threaded tip 530. K-wire guide 550 also features a handgrip 560, shaft 570, and tip 580. Additionally, K-wire guide 550 features a split ring 575 set into a circular groove 578 on the shaft 570 in close proximity to the handgrip 560.

K-wire guide 550 is inserted into and assembled with drill guide 500 such that handgrip 560 resides over handgrip 510, shaft 570 resides within shaft 520, and tip 580 proximate to tip 530. When the K-wire guide 550 is inserted into the drill guide 500, the split ring 575 enters an opening (not shown) in the handgrip 510 of the drill guide 500 and compresses, thus providing friction between the drill guide 500 and K-wire guide 550. This friction facilitates a secure connection between the drill guide 500 and K-wire guide 500, and prevents the K-wire guide 550 from inadvertently separating from the drill guide 500.

Threaded tip 530 enables drill guide 500 to be screwed into threaded through-holes 366-370 in the head 310 of plate 300. Such rigid attachment of the drill guide 500 to the plate 300 improves the dynamics of holding a drill guide in position while drilling, and the accuracy of drill hole trajectories. Alternatively, threaded tip 530 may be threadably attached to holes 466-470 in block 400, wherein these holes may be formed with threads to accept tip 530. The aid of block 400 in guiding drill guide 500 to a threaded hole in the head 310 of plate 300, and maintaining drill guide 500 in position, will be discussed in more detail, below.

Figure 11:
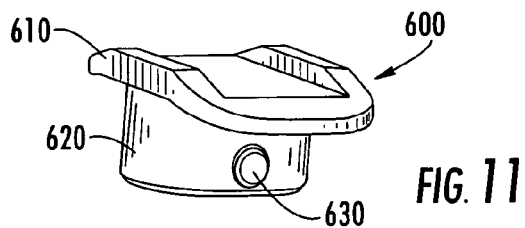
FIG. 11 is a side perspective view of a cable plug used in conjunction with a bone plate to facilitate positioning cerclage cables on the plate.

FIG. 11 illustrates a preferred embodiment of a cable plug 600 of the present invention. Cable plug 600 has a cap 610 and shank 620. The purpose of the cable plug 600 is to attach to a hole located in the stem 330 of bone plate 300 after the bone plate 300 is implanted, and thereby provide a precise and stable platform for wires or tissues to be attached thereto and prevent the wires from sliding down along the longitudinal axis of the plate.

Cable plug 600 preferably has a bead 630 associated with its shank 620 that prevents the plug 600 from separating from the plate 300 when the plate 300 is manipulated. The bead 630 is preferably made of nylon, but other suitable materials are envisioned. Additionally, other shapes and configurations of the bead 630 with respect to the plug 600 for the purpose of retaining plug 600 in a hole of the plate 300 are also envisioned.

FIGS. 12-15 illustrate a preferred embodiment of a handle 700 of the present invention. Handle 700 has a top portion 710, a shell 720, and a bottom portion 730. The shell surrounds the substructure of handle 700 and is attached to the substructure via screw 734.

The shell 720 has a series of steps 722 formed by successive circumferentially interrupted extensions 724 and recesses 726 along its height. The purpose of the shell 720 is to provide a gripping surface for a surgeon's hand. The purpose of the steps 722 is to provide an engagement surface to the head 110 of the trial component 100 of FIGS. 1 and 2. More specifically, handle 700 can fit through the opening 130 in the trial component 100, and the tongue 142 of the slider 140 of the trial component 100 together with oppositely oriented edge 135, can fit inside a circumferentially interrupted recess 726 of the handle 700 such that the tongue 142 is captured in recess 726 on one side of the handle 700 and the edge 135 is captured in recess 726 on the other side of the handle 700. Because the slider 140 is biased in the closed position as previously discussed, the tongue 142, and consequently the edge 135, exert a compressive force on the recess 726 and thus aid in holding the trial component 100 in place on the selected step of the handle 700. Further positioning and manipulation of the trial component 100 on the handle 700 will be discussed, below.

The bottom 730 of the handle 700 has an interface section 732 which interacts with the extension 480 of block 400 of FIGS. 7-9. The interface section 732 provides geometric features that mate with extension 480 of block 400 so as to removable attach the handle 700 to the block 400. The handle 700 is detached from the block 400 via the use of plunger 740.

The attachment and detachment aspects will be discussed in more detail with particular reference to FIGS. 13-15 herein.

Figure 12:
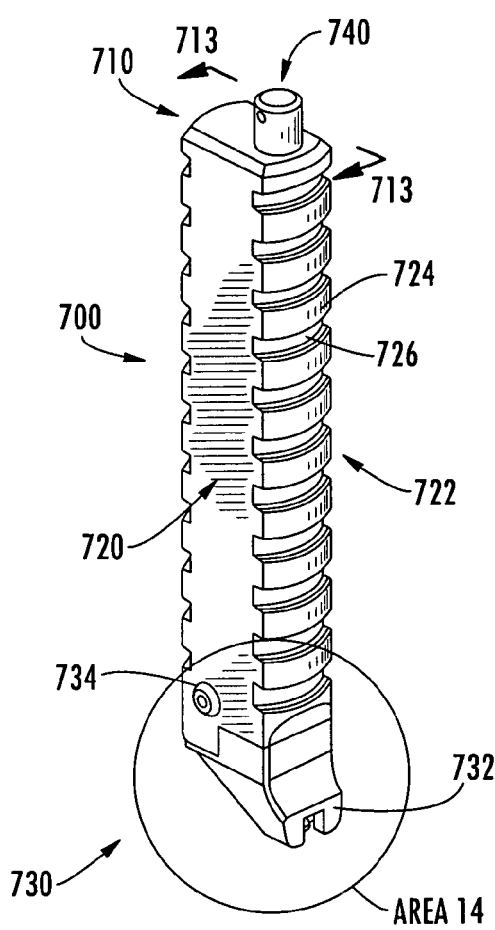
FIG. 12 is a side perspective view of a handle used in conjunction with an aiming block and a bone plate.
Figure 13:
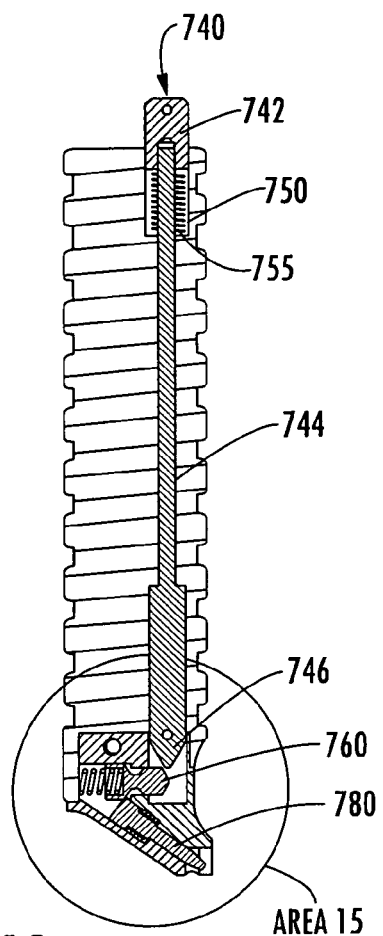
FIG. 13 is a side sectional view of the handle of FIG. 12 along lines 713-713.
Figure 14:
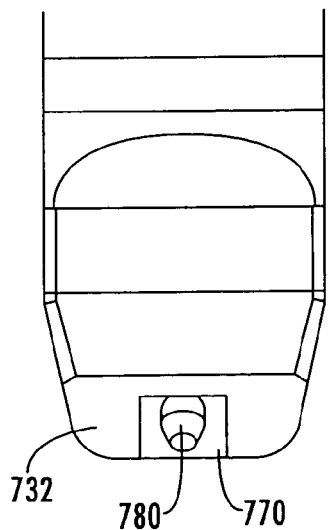
FIG. 14 is an enlarged front view of area 14 of the handle of FIG. 12.
Figure 15:
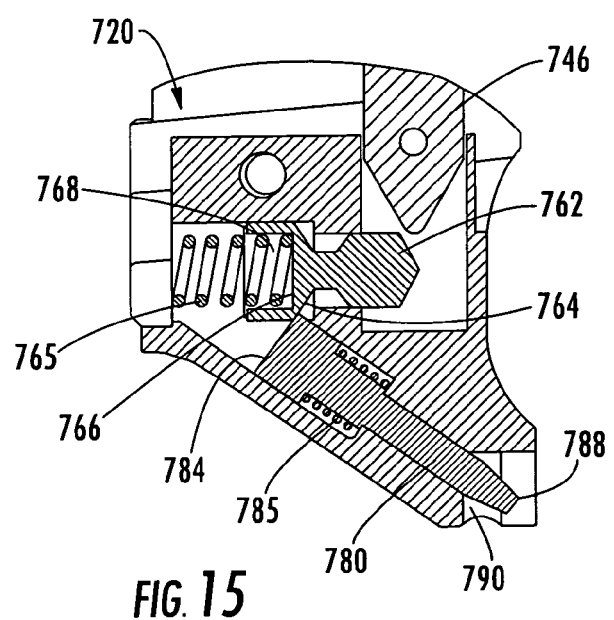
FIG. 15 is an enlarged side sectional view of area 15 of the handle of FIG. 13.

As mentioned above, FIG. 13 is a side cross-sectional view of the handle 700 along lines 713-713 of FIG. 12, FIG. 14 is an enlarged view of circular area 14 identified in FIG. 12, and FIG. 15 is an enlarged view of circular area 15 in FIG. 13. With reference to FIGS. 13-15, plunger 740 has a cap 742. The cap 742 is attached to a shaft 744, which terminates at the bottom 730 of the handle 700 in the shape of an angled plunger tip 746. Plunger 740 is biased in the upward position by spring 755 in housing 750. Tip 746 is in communication with a plug 760, and plug 760 is in communication with a pin 780 that protrudes into housing 770. More specifically, plug 760 has a plunger face 762 that contacts plunger tip 746, a pin face 764 that contacts a plug face 784 of pin 780, a spring face 766 that contacts a spring 765 which provides the biasing force to plug 760, and a spring housing 768 which, in part, houses the spring 765. Plug 760 is spring biased towards plunger tip 746 and pin 780 by spring 765 that is located behind the plug 760. Additionally, a spring 785 located around the shaft of the pin 780 provides a biasing spring force that helps keep the pin tip 788 protruding in the housing 770, as is shown in detail in FIG. 15. Springs 755 and 785 are weaker than spring 765, and as recognized by those skilled in the art, the three springs 755, 765 and 785 facilitate the intended movements of the respective parts of the handle 700 as described herein.

It is noted that housing 770 has two grooves 790 on either side of pin tip 788, but the applicability of the grooves 790 and housing 770 will be discussed in more detail below in conjunction with the interaction between the handle 700 and the block 400.

FIGS. 12 and 13 show the handle 700 in the un-actuated position, i.e., the position in which the handle 700 would be locked to the block 400. This position is defined by the plunger cap 742 protruding from the top 710 of the handle 700, and pin tip 788 protruding in housing 770. In order to actuate the handle 700 and place it to the actuated position, a downward force is exerted by a user on plunger 740. As the plunger 740 is moved downwardly, the plunger cap 742 is moved into a space 750 in the substructure of the handle 700 thus compressing spring 755, and the plunger tip 746 is moved downwardly against plunger face 762 of the plug 760, thus pushing the plug 760 backwards against spring 765. As the plug 760 moves backwards, the force exerted by pin face 764 on plug face 784 is removed, thereby allowing the pin 780, through exertion of upward force on pin 780 from pin spring 785, to be readily retracted from housing 770.

Figure 16:
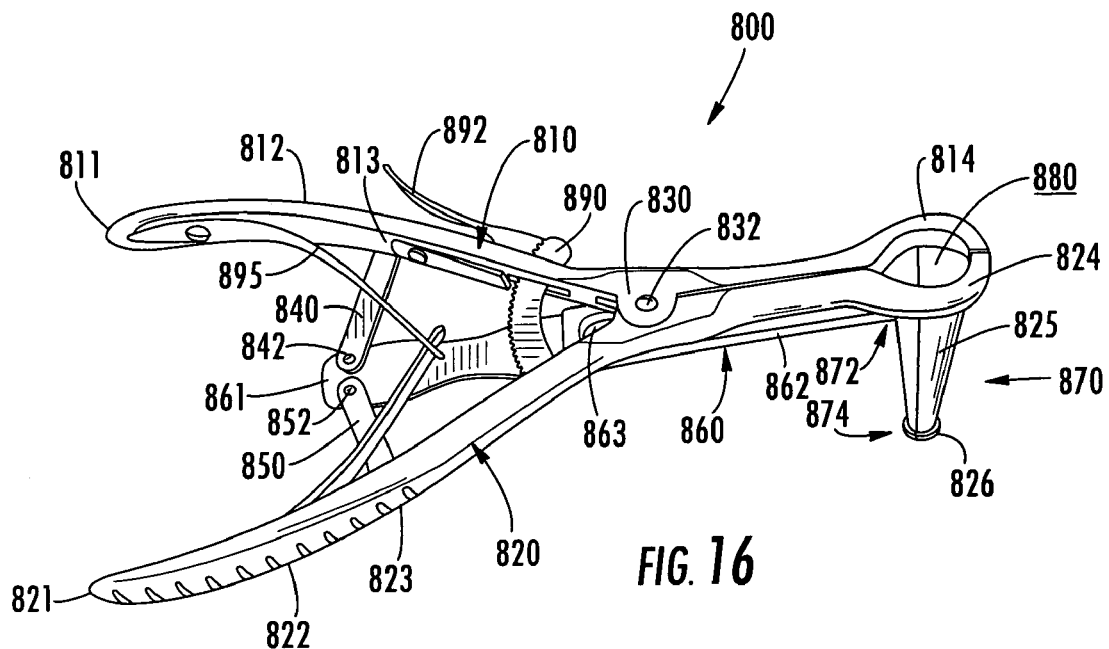
FIG. 16 is a top perspective view of a tissue spreader used for enlarging an incision, where the tissue spreader is in the closed position.
Figure 17:
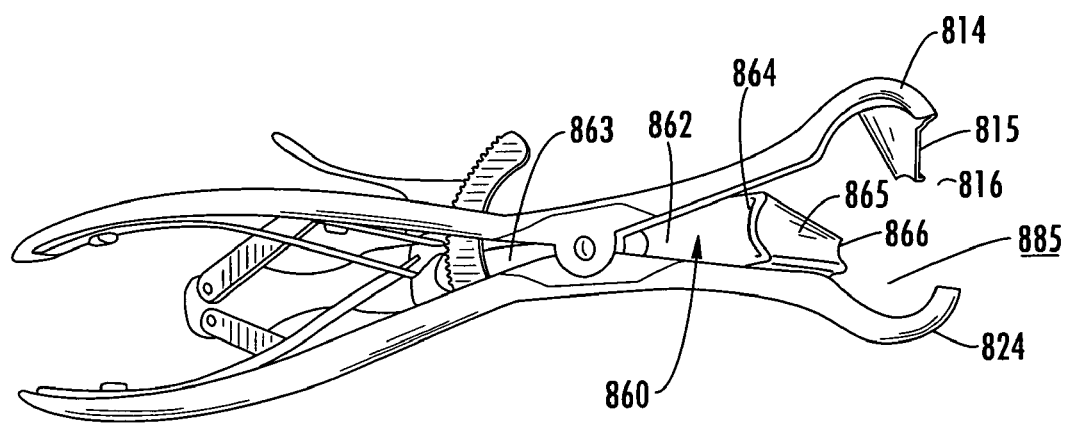
FIG. 17 is a top perspective view of the tissue spreader of FIG. 16, where the tissue spreader is in the expanded position.

FIGS. 16 and 17 illustrate a preferred embodiment of a tissue spreader of the present invention. Tissue spreader 800 generally comprises a left handle 810, a right handle 820, a left bar 840, right bar 850, and a center bar 860, and a ratchet 890, and leaf springs 895.

Left handle 810 has an end 811, a handgrip section 812, a left link pivot point 813, a curved head 814, and a blade 815 with a lip 826 on its distal end. Blade 815 is shaped in the form of a tapered frusto-conical section, is oriented generally transversely to the left handle 810, and is attached to the head 814 of left handle 810.

Right handle 820 has an end 821, a handgrip section 822, a right link pivot point 823, a curved head 824, and a blade 825 with a lip 826 on its distal end. Blade 825 is shaped and oriented similarly to blade 815, and is attached to the head 824 of right handle 820.

The left and right handles 810 and 820 are attached to each other at a handle hinge joint 830 which is formed by a guide pin 832 traversing through both handles 810 and 820.

Left bar 840 is connected to left handle 810 at pivot point 813, and connected to center bar 860 at pivot point 842. In turn, right bar 850 is connected to right handle 820 at pivot point 823, and connected to center bar 860 at pivot point 852. As will be recognized by those skilled in the art, pivot points 813, 823, 842 and 852 may be formed with pin connections, or other suitable means for facilitating the intended motion described herein.

Center bar 860 comprises a tail 861, body 862, slot 863, curved head 864, and blade 865. Blade 865 is shaped and oriented similarly to blades 815 and 825, and is attached to the head 864 of center bar 860. The slot 863 of the center bar 860 is cooperatively arranged with guide pin 832 such that pin 832 rides inside slot 863 and does not separate from slot 863. As mentioned above, the tail 861 of center bar 860 is attached to left bar 840 at pivot point 842 and to right bar 850 at pivot point 852.

Ratchet 890 is connected to right handle 820, penetrates left handle 810, and is cooperatively arranged with pawl 892. Leaf spring 895 is attached to both the left and right handles 810 and 820 and provides an outward biasing force on the left and right handles 810 and 820 in the areas of the left and right ends 811 and 821 of the handles. As is well known in the art, the combination of ratchet 890, pawl 892 and leaf springs 895 facilitates placing and maintaining the tissue spreader 800 in either the open or closed position, or any position therebetween. Of course, other ratchet, pawl and spring configurations, as well as various combinations thereof that are well known in the art, are also contemplated for incorporation with the tissue spreader 800 to perform the same functions as described above.

With reference to FIG. 16, tissue spreader 800 is in the closed position, as identified by blades 815, 825 and 865 being positioned closely together, thus forming a tube 870. Tube 870 has a proximal end 872, which is where each blade 815, 825 and 865 is attached to its respective head 814, 824 and 864, and a distal end 874 opposite the proximal end, where lips 816, 826 and 866 form a collar. Tube 870 forms a passage 880 wherein the distal end 874 has a smaller internal cross-section than the proximal end 872.

As will be recognized by those skilled in the art, the arrangement of left handle 810 with right handle 820, as well as with left bar 840, right bar 850 and center bar 860, forms a linkage which facilitates movement of left handle 810, right handle 820 and center bar 860 simultaneously upon application of compressive forces on hand grip sections 812 and 822 of the left and right handles 810 and 820, respectively.

With reference to FIG. 17, when tissue spreader 800 is gripped by a user's hand, and a compressive force is exerted on hand grip sections 812 and 822 to urge them toward each other through the established connection points and linkages described above, tube 870 expands via left and right blades 815 and 825 moving away from each other, while center bar 860 gets drawn in the direction of ends 811 and 821 of the tissue spreader 800, thus drawing center blade 865 away from blades 815 and 825. As this occurs, when the tube 870 is within an incision in a patient that is to be expanded, lips 816, 826 and 866 facilitate engaging, spreading and retaining tissue in the expanded position. The result is a passage 885 which is larger than passage 880. At this point, tissue spreader 800 is in the open position.

As will be recognized by those skilled in the art, the materials used for all of the above-mentioned instruments and implants must be compatible with surgical usage as well as with the intended purposes of the instruments and implants, thereby accounting for such things as corrosion resistance, stress, strain, rigidity, weight, tactility and even disposability.

For example, implants such as plates 300 and 300A-300E are typically made from surgical grade stainless steel and titanium, but other materials such composites or biodegradable and non-biodegradable polymers are also envisioned. Instruments such as the trial 100, drill guide 500, handle 700, and tissue spreader 800 may, similarly, be made from stainless steel, from any other appropriate, sufficiently rigid and strong material or composite, or combinations thereof, as well as from a material, or materials, that facilitates economical disposability of the instrument.

The following discussion will be directed to the methods, usage and interactions of the various implants and instruments, as described above. Although the discussion involves working with a fracture of a distal femur, it is well recognized by those skilled in the art that the methods, usages and interactions described herein may be readily adapted for fractures of other bones.

Figure 18:
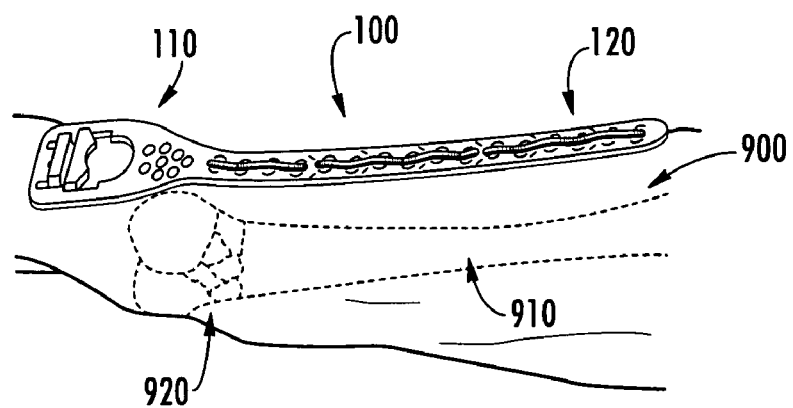
FIG. 18 is a top isometric plan view of the trial component of FIG. 1 positioned over a leg having a fractured distal femur, for preoperative assessment and planning of the fixation procedure.

With reference to FIG. 18, preoperative assessment and planning of fracture fixation surgery begins with placement of the trial 100 over the leg 900 of a patient. The Trial 100 is oriented in the same general direction as the femur 910, such that the head 310 of the trial overlays the metaphysis, and the stem 120 overlays the diaphysis. One side of the trial 100 is used in conjunction with work on a left femur while the other side is used in conjunction with work on a right femur.

Next, a fluoroscopic image of the fracture area 920 is generated. The image shows the trial 100 overlaying the femur 910 and the fracture 920. Because all the markers 160, 171-174, and 180-186 on the trial 100 are radiopaque, they are visible on the image. Thus, a surgeon may preoperatively select the desired length of bone plate 300 to be used based on markers 180-186 overlaying the femur 910. Additionally, hole markers 160-174 aid the surgeon in visualizing screw positions on the femur 910 based on the plate 300 that is to be implanted, as well as aid the surgeon in deciding where to use locking inserts for either monoaxial or polyaxial screws along the stem 330 of the plate 300.

Once the surgeon determines the desired size of the plate 300 that will be implanted, as well as the general position of where it will be located relative to the fracture 920, the surgeon selects that sized plate from a kit of variously sized distal femoral plates. The surgeon then also selects the proper block 400 for use with that plate. The blocks 400 are either configured for a right plate or a left plate, but fit every length of the left or right plate.

The plates are pre-contoured. However, once the desired plate 300 is selected, the surgeon may, optionally, further bend the plate to better conform it's shape to the particular anatomy of the bone at the implantation site. In so doing, care must be taken, however, since bending of plate 300 in the regions of the head 310 and neck 320 may affect the ability to correctly seat inserts and/or locking screws into those areas of the plate 300.

Block 400 is positioned over head 310 of plate 300 such that the end 412 of the block 400 is oriented generally over the end 312 of the plate 300. Block 400 is then attached to the head 310 of plate 300 by inserting a small screw (not shown) through hole 450 in the block 400, and threading the screw into hole 350 in plate 300. Block 400 is securely held in place on plate 300 because of this screw, but also because of the shape of the chamfer 445 of the block 400 matching and mating with the chamfer 315 of the top surface 314 of the head 310 of the plate 300. Advantageously, the block 400 and plate 300 may be designed such that when they are assembled, there is a small gap between the bottom surface 440 of the block 400, and top surface 314 of the plate 300. This is done so as to allow for manufacturing variations in the two parts.

Next, with reference to FIG. 19, handle 700 is attached to block 400. This is accomplished by positioning the handle 700 proximate to, and slightly above, the extension 480 of the block 400 such that interface section 732 faces extension 480. Without the need for depressing plunger 740, the handle 700 is then slipped over the extension 480 such that extension 480 enters and rides up into housing 770. This motion is guided by virtue of rails 482 and 484 moving along grooves 790. As this occurs, pin tip 788 rides in sloped channel 486, and is pushed back into the housing 770 by the sloped channel 486. As the sloped channel 486 moves higher into the housing 770, pin tip 788 encounters dimple 488, and pops into it by virtue of the biasing force exerted on the pin 780. This action, along with the cooperative assembly of the rails 482 and 484 in the grooves 790, serve to lock the handle 700 to the block 400, and consequently to the plate 300.

The handle 700 may be separated from the block 400 at any time by depressing the plunger 740, and then moving the handle 700 such that the housing 770 moves out of engagement with the extension 480 of the block 400. In depressing the plunger 740, the resulting motion of internal parts of the handle 700, as described above, allows the pin to be pushed back into the housing 770 as the dimple 488 is moved downwardly and away from pin tip 788.

Intraoperatively, an initial incision is made in the metaphyseal area. In a regular surgical technique, this incision may be as long as the plate 300. In minimally invasive surgery, this incision may by approximately as long as the head 310 of the plate 300.

In either regular or minimally invasive surgery, to facilitate easier insertion and manipulation of the plate 300 within the incision, it is preferable to have handle 700 attached to block 400. Plate 300 is then inserted through the incision and positioned against the femur 910 in a desired orientation through manipulation of handle 700, without the need for directly holding and moving plate 300, itself. In the case of minimally invasive surgery, prior to insertion of the plate 300, it is preferable to first insert the tissue elevator 200 into the incision to create a pathway for the implant to follow, thus facilitating smoother insertion of the implant while minimizing tissue damage in the process.

As is known and recognized in the art, the use of fluoroscopy, or any other imaging process, may be used at any time during this procedure, as deemed appropriate, to provide feedback imaging as to the orientation of the plate 300 versus the femur 910.

It is further noted that one of the differences between the open and MIS approaches discussed herein is that the MIS approach involves the use of the trial 100 after the plate 300 is inserted into position on the bone, in order to aid in placement of screws through the stem 330 of the plate 300, while the open approach does not since the open incision enables full visualization of the plate 300 including the stem 330. This and other differences between the MIS and open approach will be recognized to those skilled in the art, from further discussion, below.

Figure 20:
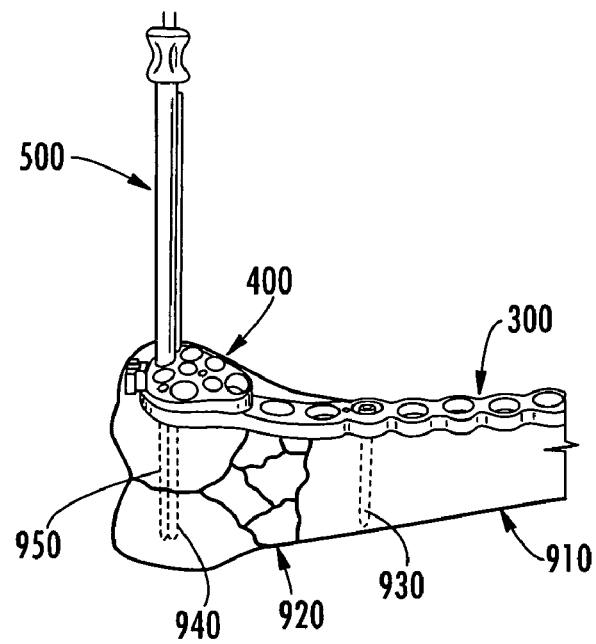
FIG. 20 is a side perspective plan view of a drill guide, aiming block and plate positioned on a fractured distal femur, with a first bone screw positioned through the plate, and a screw hole being drilled for another screw, while a K-wire is positioned through the plate and in the bone.

With reference to FIG. 20, after insertion of the plate 300, preferably, a first screw 930 is then placed in the slot 360 of the plate 300, through the initial incision. As is known in the art, the process of screw placement is accomplished by using a drill guide to guide a drill bit in forming the appropriate hole, optionally tapping the hole (unless using self-tapping screws), and then inserting the desired screw. For regular screws, a regular drill guide would be used. For locking screws, drill guide 500 may be used.

Placement of this first screw 930 in the neutral position of slot 360 enables a surgeon to readily readjust the plate 300 prior to final fixation. Although it is preferable to use slot 360 because of the added degree of freedom of movement, initial screw placement will also be dictated by the location of the fracture lines, as well as the anatomy and suitability of the bone for retaining the first screw 930.

Next, preferably, K-wires 940 are driven through holes 461 and 462 of block 400 and corresponding holes 361 and 362 of the plate 300, into the femur 910 to temporarily hold the head 310 of the plate 300 against the femur 910. K-wires 940 can also be inserted through any locking holes using the drill guide 500 mounted with the K-wire guide 550 as shown in FIG. 10.

Once the desired orientation of the plate 300 on the femur 910 is established, screws are used to fix the head 310 of the plate 300 to the femur 910. This process may, preferably, be initiated by inserting a regular drill guide in opening 463 of block 400, and drilling, with a drill bit 950, an appropriately sized pilot hole in the femur 910 that is then tapped if necessary. Finally, a regular screw, such as a lag screw, may be inserted into opening 463, and screwed down to tighten the head 310 of the plate 300 against the femur 910.

As noted earlier, openings 466-470 in the block 400 have set trajectories that correspond to the openings 366-370 in the head 310 of the plate 300. The thickness of block 400 provides a depth dimension to the openings of the block 400 such that the correct trajectory of the drill guide is established once the drill guide is inserted into one of the openings. Of course, for the block that is used with polyaxial screws, the openings in the block are conical and thus facilitate selecting desired trajectories for the screws.

Next, preferably, regular screws are similarly inserted and affixed through holes 464/364 and 465/365 of the block 400 and plate 300. Thereafter, preferably, locking screws are inserted and affixed through holes 466/366, 467/367, 468/368, and 469/369 of the block 400 and plate 300.

As mentioned earlier, for locking screws, drill guide 500 may be used to prepare the screw holes. This is done by inserting the drill guide 500 through hole 466, for example, and threading the drill guide tip 530 into the threaded hole 366 in the head 310 of the plate 300. Such connection provides accurate and rigid positioning of drill guide 500 for use in drilling appropriate pilot holes for locking screws. Once the pilot hole is drilled, drill guide 500 may be disengaged from the plate 300, so that screw placement may proceed.

In attaching the stem 330 of the plate 300 to the femur 910, the surgeon has the option to select which holes 355, 371-378 of the plate 300 will receive locking screws. Once the desired holes are selected, the surgeon then places threaded inserts, as discussed previously, into these holes, so that locking screws may then be placed therethrough. The placement of locking screws is facilitated by using drill guide 500, as described above. Namely, drill guide 500 is threadably attach to the threaded insert, and guides a drill bit to form a pilot hole which will then accept a locking screw.

The placement of threaded inserts may be done at any time, intra- or preoperatively, but preferably, is done preoperatively. One reason for doing so is to facilitate optimization and efficiency of the intraoperative procedure. Another is to facilitate a MIS approach.

To aid in placement of a threaded insert into a hole in the stem 330 of the plate 300, an inserter instrument (not shown) is available to facilitate insertion. The distal end of the inserter instrument locks onto the insert, and the proximal end provides a gripping surface to enable a surgeon to easily manipulate and attach the threaded insert to the plate 300. Once the threaded insert is attached to the plate 300, the inserter instrument is disengaged from the insert, and further procedures to implant a locking screw may be undertaken, as previously discussed. If removal of the insert is required because it is placed in the wrong hole, for example, then an extractor instrument may be used. Such inserter and extractor instruments are disclosed in U.S. Patent Application entitled "An Extractor For A Bone Connection Element", with inventors Stefan Kugler, Roland Thomke, André Gasser and Christian Lutz, filed Nov. 30, 2004, the entire disclosure of which is incorporated herein by reference as if fully set forth herein.

As mentioned earlier, in regular open surgery, an incision that generally spans the length of the entire plate 300 is made in the tissue, particularly in order to provide visualization of the stem 330 of the implant for purposes of properly drilling, optionally tapping, and inserting screws therethrough. With such an incision, the above-discussed steps of plate implantation may be carried out through direct visualization, until all the desired screws are in place.

Figure 21:
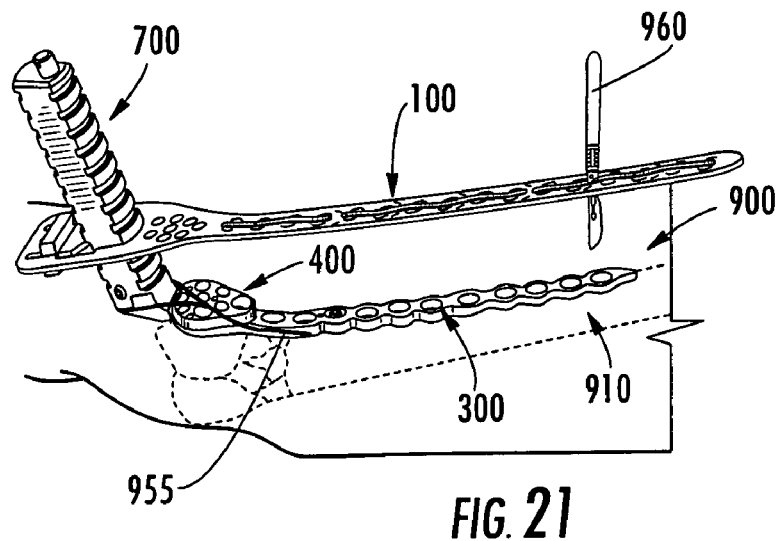
FIG. 21 is a side perspective plan view of a trial component, handle, aiming block and plate positioned over a fractured distal femur, and a scalpel being used to make an incision in the leg of a patient through the trial component, where the incision corresponds to a position of a screw that is to be applied to attach the bone plate to the femur.

In minimally invasive surgery, such a long incision is undesirable. With reference to FIG. 21, for MIS, the initial incision 955 need only be as long as the head 310 and neck 320 of the plate 300 for direct visualization of same. Once the head 310 and neck 320 of plate 300 are attached per the procedures discussed above, in accordance with the preferred MIS procedure the trial 100 is then placed on handle 700.

Placing the trial 100 on the handle 700 requires retracting the slider 140 on the trial 100 to enlarge opening 130, holding the slider 140 in this open position, and slipping the handle 700 through the enlarged opening 130. In so doing, the trial 100 is positioned over the femur 910, and lowered along the handle 700 until it comes to rest against the leg 900. Once there, the slider 140 may be released and allowed to move back to its biased closed position. It should be assured that in the closed position, the slider 140 and edge 135 reside in one of the recesses 726 on the shell 720 of the handle 700, to ensure a snug connection. Therefore, if the slider 140 is not initially in such a position, the trial 100 may be moved either upwardly or downwardly along the handle 700 until edge 135 is seated and slider 140 clicks into place.

With the trial 100 attached to the handle 700, the surgeon may select in which holes 371-374 of the plate 300, for example, to place screws by looking at corresponding hole markers 171-174 on the stem 120 of the trial 100, and with a scalpel 960, making a small incision 970 in the tissue by cutting through the appropriate slot 150, 151, or 152 in the plate in the area of the desired hole marker. For example, if a screw were to be implanted in hole 371, then the incision would be made in the area of marker 171 through slot 150.

Once this incision 970 is made, the trial 100 may, optionally, be either removed from the handle 700, or preferably, rotated out of the way of the incision 970. The biased slider 140 and edge 135 enable rotation of the trial 100 in recess 726 while preventing the trial 100 from moving up or down the handle 700 to another recess.

Figure 22:
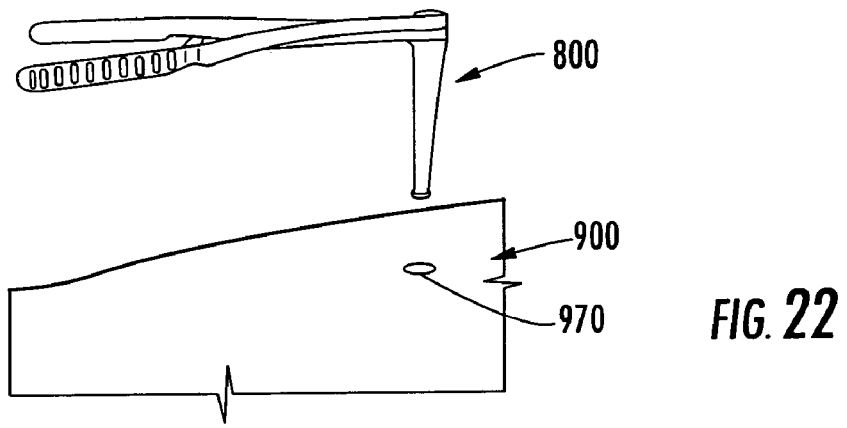
FIG. 22 is a side perspective plan view of a tissue spreader of FIG. 16 positioned over the incision of FIG. 21.
Figure 23:
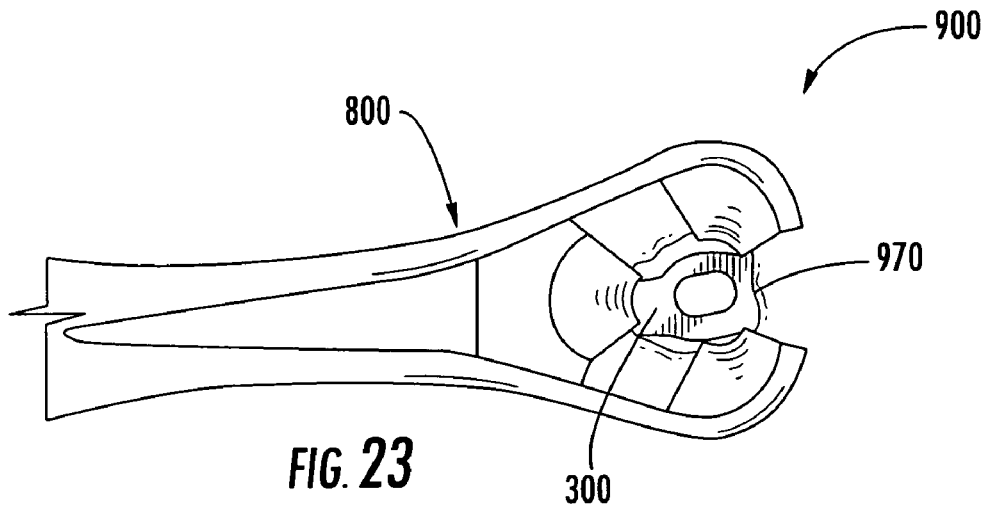
FIG. 23 is a top view of the tissue spreader of FIG. 16 positioned inside the incision of FIG. 21 and expanded to enlarge the passage in the tissue so as to visualize the plate hole that will receive the bone screw.

With reference to FIGS. 22 and 23, when the trial 100 is positioned out of the way, incision 970 is exposed. Since incision 970 is small, preferably, a tissue spreader 800 may be used to enlarge the incision 970. This is done by inserting the tube 870 of the tissue spreader 800 into the incision 970, and opening the incision 970 by compressing the handles 810 and 820 to spread apart the blades 815, 825 and 865, thereby enlarging the incision and facilitating visualization of the hole in the plate 300 into which a screw will be implanted. Implantation of a screw may be conducted through the open passage 890 of the tissue spreader 800 using the techniques discussed above.

Once the screw is implanted, the tissue spreader 800 is closed and removed from the incision 970. The trial 100 is then placed back over the femur 910, and the MIS incision and screw implantation procedure repeated for each additional screw that is desired to be implanted.

Figure 24:
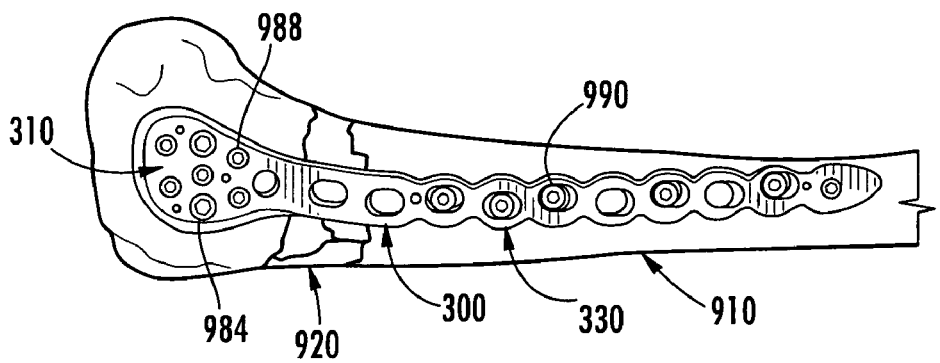
FIG. 24 is a side perspective plan view of the bone plate of FIG. 4 attached to the distal fractured femur with various bone screws.
Figure 25:
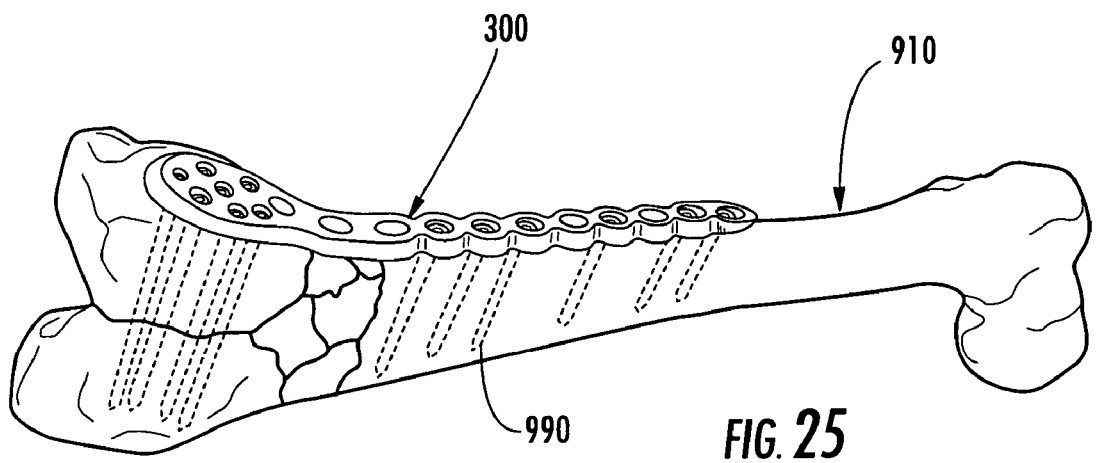
FIG. 25 is a top perspective plan view of the arrangement of FIG. 24 with the bone screws being shown within the femur.

FIGS. 24 and 25 illustrate the result of either of the open or MIS surgical procedures discussed above, wherein plate 300 is affixed to a femur 910 over a fracture 920 via various screws in the head 310 and stem 330 of the plate 300, such as regular screw 984 and locking screw 988 in the head 310, and regular screw 990 in the stem 330.

Figure 26:
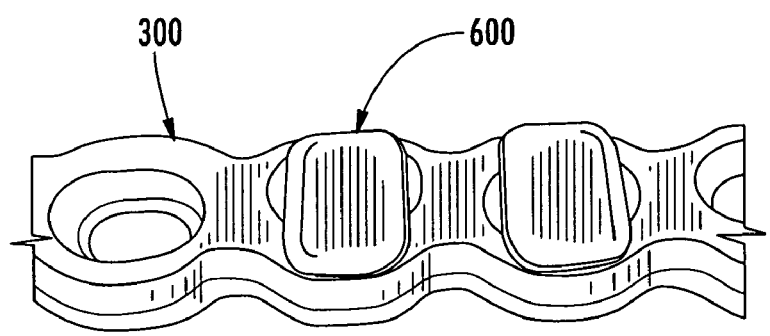
FIG. 26 is a side perspective plan view of a bone plate together with cable plugs mounted in two bone screw holes.

FIG. 26, illustrates a bone plate 300 with cable plugs 600 attached over select screw holes. Once the fixation of plate 300 to the femur 910 is complete, cable plugs 600 may optionally be attached to select holes of the plate 300 to provide a precise and stable platform for cables or wires to be attached thereto.

Having described the various implants, instruments, and methods of the present invention, it is understood that numerous variations in structures, materials, functions and methods may be made by those skilled in the art without deviating from the sprit and scope of the invention. For example, numerous variations of trial, plate and block shapes, sizes and material properties may be formed and used in conjunction with various fractures of different bones. Additionally, plastics or other appropriate materials may be used to make the various instruments more readily and economically adapted for disposability. Still further, the selection of regular screws versus locking screws, as well as the sequence of screw insertion may vary depending on such things as surgical conditions, anatomies and surgeon preferences.

Although the present invention has been described with reference to the particular embodiments herein, it is not intended that the invention be limited thereto, as it is intended that the invention be as broad in scope as the art will allow and that the specification be read likewise. It will therefore be appreciated by those skilled in the art that yet other modifications could be made to the invention without deviating from its spirit and scope as so claimed.

The invention claimed is:

1. A component for placement adjacent a bone to aid in selecting a bone plate from a plurality of bone plates, said component comprising:
   a head portion made at least in part from a radiolucent material; and
   an elongate stem portion extending from said head portion along a centerline and made from a radiolucent material, said stem portion having first radiopaque markers located on the elongate stem radiolucent material indicating lengths of at least two plates of said plurality of bone plates and having a plurality of second radiopaque screw hole markers located on the elongate stem radiolucent material on either side of a slot in the elongate stem along a portion of the centerline wherein said head portion includes a connection for receiving a handle and further comprising a locking element adjacent said opening, said locking element adapted for engaging said handle wherein said locking element is a slider element slidably connected with said component and moveable with respect to said head portion into engagement with said handle.

2. The component of claim 1, wherein said connection is an opening.

3. The component of claim 1, wherein said handle is rotatable within said opening.

4. The component of claim 1, wherein said slider element has an open position defined by said opening being larger, and a closed position defined by said opening being smaller.

5. The component of claim 4, wherein said slider element is biased towards said closed position which is adapted for attaching said component to said handle.

6. The component of claim 4, wherein said open position of said slider element allows movement of said handle through said opening.

7. The component of claim 1, wherein said slider element further comprises a tongue and a tab, and is generally parallel to said component.

8. The component of claim 7, wherein said tongue is generally transversely oriented to said tab, and generally parallel to said component.

9. The component of claim 1, wherein said stem portion further comprises at least one slot surrounded at least in part by the second markers indicating positions of screw holes in said bone plate.

10. The component of claim 9, wherein a centerline of said slot is defined by centers of at least two adjacent of said second markers indicating positions of screw holes.

11. The component of claim 1, wherein said head and stem portions are formed as a longitudinally extending plate having a shape generally corresponding to a longitudinal shape of a long bone.

12. The component of claim 1, wherein said head and stem portions have a first side facing towards said bone and a second side facing away from said bone, and wherein said first side aids in selecting a right bone plate, and said second side aids in selecting a left bone plate.

13. A component that facilitates making an incision corresponding to a screw hole in a bone plate that is to be affixed to a fractured bone, said component comprising:
a head portion and an elongate radiolucent stem portion, said stem portion having a longitudinally extending slot and a plurality of first and second arcuate radiopaque hole markers on the surface of the radiolucent material of the stem portion indicating positions of corresponding holes in said bone plate, the first and second arcuate radiopaque hole markers located on opposite sides of the slot with concave portions of the first and second members facing each other wherein said head portion includes a connection for receiving a handle further comprising a locking element adjacent said opening, said locking element adapted for engaging said handle wherein said locking element is a slider element slidably connected with said trial component and moveable with respect to said head portion into engagement with said handle.

14. The component of claim 13, wherein a centerline of said slot is defined by centers of said first and second hole markers.

15. The component of claim 14, further comprising third and fourth hole markers.

16. The component of claim 15, wherein said centerline of said slot is defined by centers of said first, second, third and fourth hole markers.

17. The component of claim 16, wherein said second hole marker is not located on a line defined by said first and third hole markers.

18. The component of claim 17, wherein said first, second, third and fourth hole markers are comprised of first and second radiopaque indicators of a circle.

19. The component of claim 18, wherein said first and second visible indicators of said first, second, third and fourth hole markers are on opposite sides of said slot.

20. The component of claim 13, wherein said slot is not straight.

21. The component of claim 13, further comprising multiple slots and more than two hole markers.

22. The component of claim 13, further comprising a radiopaque plate length marker on said stem indicating a length of a bone plate.

23. The component of claim 22, further comprising multiple plate length markers.

24. The component of claim 13, wherein said connection is an opening.

25. The component of claim 24, wherein said handle is rotatable within said opening.

26. The component of claim 13, wherein said slider element has an open position defined by said opening being larger, and a closed position defined by said opening being smaller.

27. The component of claim 26, wherein said slider element is biased towards said closed position which is adapted for attaching said component to said handle.

28. The component of claim 26, wherein said open position of said slider element allows movement of said handle through said opening.

29. The component of claim 13, wherein said slider element further comprises a tongue and a tab, and is generally parallel to said component.

30. The component of claim 29, wherein said tongue is generally transversely oriented to said tab, and generally parallel to said component.

31. The component of claim 13, wherein said head and stem portions have a first side facing towards said bone and a second side facing away from said bone, and wherein said first side aids in selecting a right bone plate, and said second side aids in selecting a left bone plate.

32. A method of locating a position for an incision and providing for the incision to be made, comprising:
providing a radiolucent component having a centrally located slot and at least two individual radiopaque hole markers, one marker located on either side of the slot indicating positions of corresponding holes in a subcutaneously located bone plate;
releasably adjusting said component relative to said bone plate so as to be located above the skin; and
making an incision through said slot corresponding to a selected one of said at least two hole markers.

33. The method of claim 32, further comprising after providing said component, coupling a handle to said bone plate.

34. The method of claim 33, further comprising coupling said component to said handle prior to making said incision.

35. The method of claim 34, further comprising moving said component away from said incision after said incision is made.

36. The method of claim 35, wherein moving said component away from said incision comprises rotating said component on said handle.

37. The method of claim 35, wherein moving said component away from said incision comprises uncoupling said component from said handle.

38. The method of claim 35, further comprising inserting a tissue spreader into said incision and spreading said incision with said tissue spreader.

39. The method of claim 38, further comprising preparing a bone screw hole in a fractured bone through said incision, and inserting a bone screw to attach said bone plate to said fractured bone.

40. The method of claim 33, wherein coupling said handle to said bone plate comprises coupling a block to said bone plate, and coupling said handle to said block.

41. The method of claim 40, further comprising affixing said bone plate to a fractured bone using screws.

42. The method of claim 41, further comprising uncoupling said block from said bone plate and removing said block via manipulation of said handle to which said block is coupled.

43. A method of locating a position for an incision and providing for the incision to be made, comprising:

provided a component having a slot and at least two hole markers indicating positions of corresponding holes in a subcutaneously located bone plate;

releasably adjusting said component relative to said bone plate;

making an incision through said slot corresponding to a selected one of said at least two hole markers;

further comprising after providing said component, coupling a handle to said bone plate;

further comprising coupling said component to said handle prior to making said incision;

wherein releasably adjusting said component relative to said bone plate comprises adjusting said component along a height of said handle.

* * * * *

UNITED STATES PATENT AND TRADEMARK OFFICE
CERTIFICATE OF CORRECTION

PATENT NO. : 7,648,508 B2  Page 1 of 1
APPLICATION NO. : 10/999665
DATED : January 19, 2010
INVENTOR(S) : Lutz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1384 days.

Signed and Sealed this

Twenty-third Day of November, 2010

David J. Kappos
*Director of the United States Patent and Trademark Office*